(12) United States Patent
Eki

(10) Patent No.: US 11,643,014 B2
(45) Date of Patent: May 9, 2023

(54) IMAGE CAPTURING DEVICE AND VEHICLE CONTROL SYSTEM

(71) Applicant: Sony Semiconductor Solutions Corporation, Kanagawa (JP)

(72) Inventor: Ryoji Eki, Kanagawa (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 153 days.

(21) Appl. No.: 17/263,116

(22) PCT Filed: Jul. 31, 2019

(86) PCT No.: PCT/JP2019/030097
§ 371 (c)(1),
(2) Date: Jan. 25, 2021

(87) PCT Pub. No.: WO2020/027233
PCT Pub. Date: Feb. 6, 2020

(65) Prior Publication Data
US 2021/0152732 A1 May 20, 2021

(30) Foreign Application Priority Data

Jul. 31, 2018 (JP) .............................. JP2018-144173
Jul. 29, 2019 (JP) .............................. JP2019-139196
Jul. 30, 2019 (JP) .............................. JP2019-140197

(51) Int. Cl.
*H04N 5/232* (2006.01)
*H04N 5/225* (2006.01)
(Continued)

(52) U.S. Cl.
CPC ....... *H04N 5/23218* (2018.08); *G06K 9/6232* (2013.01); *G06N 3/08* (2013.01);
(Continued)

(58) Field of Classification Search
CPC ............ H04N 5/23218; H04N 5/2252; H04N 5/23206; H04N 5/335; H04N 5/341;
(Continued)

(56) References Cited

U.S. PATENT DOCUMENTS 6,839,452 B1 * 1/2005 Yang ...................... H03F 3/082
348/E3.02
8,417,046 B1   4/2013 McDougal
(Continued)

FOREIGN PATENT DOCUMENTS

EP    2372308 A2   10/2011
EP    3515057 A1    7/2019
(Continued)

OTHER PUBLICATIONS

International Written Opinion dated Oct. 29, 2019 in connection with International Application No. PCT/JP2019/030097, and English translation thereof.
(Continued)

*Primary Examiner* — Timothy J Henn
(74) *Attorney, Agent, or Firm* — Wolf, Greenfield & Sacks, P.C.

(57) ABSTRACT

Fabrication processing is executed in a chip of an image sensor. An image capturing device includes an image capturing unit (11) mounted on a vehicle and configured to generate image data by performing image capturing of a peripheral region of the vehicle, a scene recognition unit (214) configured to recognize a scene of the peripheral region based on the image data, and a drive control unit (12) configured to control drive of the image capturing unit based on the scene recognized by the scene recognition unit.

17 Claims, 24 Drawing Sheets

(51) Int. Cl.
*H04N 5/341* (2011.01)
*G06K 9/62* (2022.01)
*G06N 3/08* (2006.01)
*G06V 10/46* (2022.01)
*H04N 5/335* (2011.01)

(52) U.S. Cl.
CPC ......... *G06V 10/462* (2022.01); *H04N 5/2252* (2013.01); *H04N 5/23206* (2013.01); *H04N 5/341* (2013.01); *H04N 5/335* (2013.01); *H04N 2005/2255* (2013.01)

(58) Field of Classification Search
CPC ....... H04N 2005/2255; H04N 5/23203; H04N 5/23219; H04N 5/23225; H04N 5/23229; H04N 13/239; H04N 9/64; H04N 5/232; H04N 5/232411; H04N 5/3454; H04N 5/374; H04N 5/378; H04N 5/379; H04N 9/04557; H04N 5/23245; H04N 5/2351; H04N 5/345; H04N 5/3559; H04N 5/3694; G06K 9/6232; G06N 3/08; G06V 10/462; G06V 10/10; G06V 10/12; G06V 10/25; G06V 20/58; G06V 10/22; G06V 10/82; G06V 10/955; G06V 20/56; G06V 20/693; G06V 40/166; B60R 2300/30; B60R 1/00; A61B 1/043; A61B 1/045; A61B 1/0638
See application file for complete search history.

(56) References Cited

U.S. PATENT DOCUMENTS

| | | |
|---|---|---|
| 8,610,787 B2 | 12/2013 | Namba |
| 9,883,112 B1 | 1/2018 | Igor' Valer'Evich |
| 10,071,676 B2 * | 9/2018 | Schofield ................ F21S 41/60 |
| 10,977,801 B2 | 4/2021 | Heo |
| 11,430,259 B2 | 8/2022 | Chen |
| 2010/0182447 A1 | 7/2010 | Namba |
| 2011/0262039 A1 | 10/2011 | Du |
| 2015/0085170 A1 | 3/2015 | Takeda |
| 2015/0229818 A1 | 8/2015 | Fukuyama |
| 2015/0334267 A1 | 11/2015 | Hirakawa |
| 2015/0339838 A1 | 11/2015 | Friedman |
| 2016/0005152 A1 | 1/2016 | Yang |
| 2016/0012615 A1 | 1/2016 | Gao |
| 2016/0259980 A1 | 9/2016 | Mlybari |
| 2016/0328872 A1 | 11/2016 | Hauswiesner |
| 2017/0192666 A1 | 7/2017 | McCarthy |
| 2017/0262962 A1 | 9/2017 | Rad |
| 2017/0267178 A1 | 9/2017 | Shiga |
| 2017/0313297 A1 * | 11/2017 | Okada ..................... G08G 1/16 |
| 2017/0332198 A1 * | 11/2017 | Dannenbring ............ G06T 7/73 |
| 2017/0339431 A1 | 11/2017 | Zhang |
| 2018/0075290 A1 | 3/2018 | Chen |
| 2018/0114073 A1 | 4/2018 | Zhang |
| 2018/0134290 A1 * | 5/2018 | Kataoka ............... B62D 15/025 |
| 2018/0268571 A1 | 9/2018 | Park |
| 2018/0286037 A1 | 10/2018 | Zaharchuk |
| 2018/0345953 A1 * | 12/2018 | Mizoguchi .......... B60W 10/188 |
| 2018/0357800 A1 | 12/2018 | Oxholm |
| 2019/0186931 A1 * | 6/2019 | Dittmer .................... G06T 7/70 |
| 2019/0197353 A1 | 6/2019 | Yonetsuji |
| 2019/0204448 A1 | 7/2019 | Eki |
| 2019/0279074 A1 | 9/2019 | Lin |
| 2019/0294961 A1 | 9/2019 | Zuev |
| 2019/0311202 A1 | 10/2019 | Lee |
| 2019/0377967 A1 | 12/2019 | Yabuuchi |
| 2020/0163643 A1 | 5/2020 | Desaute |
| 2020/0279354 A1 | 9/2020 | Klaiman |
| 2020/0286213 A1 | 9/2020 | Unger |
| 2020/0380683 A1 | 12/2020 | Tanaka |
| 2020/0413012 A1 | 12/2020 | Alleysson |
| 2021/0142095 A1 | 5/2021 | Shi |
| 2021/0224567 A1 | 7/2021 | Wang |
| 2021/0232806 A1 | 7/2021 | He |
| 2021/0264192 A1 | 8/2021 | Eki |
| 2021/0334942 A1 | 10/2021 | Wang |

FOREIGN PATENT DOCUMENTS

| | | |
|---|---|---|
| JP | 2015-065271 A | 4/2015 |
| JP | 2017158065 | 9/2017 |
| JP | 2018-007077 A | 1/2018 |
| WO | WO-2009001530 A1 | 12/2008 |
| WO | WO-2017187811 A1 | 11/2017 |
| WO | WO 2018/051809 A1 | 3/2018 |
| WO | WO 2018/109976 A1 | 6/2018 |

OTHER PUBLICATIONS

International Preliminary Report on Patentability dated Feb. 11, 2021 in connection with International Application No. PCT/JP2019/030097, and English translation thereof.

Bong et al., A 0.6mW Ultra-Low-Power Convolutional-Neural-Network Face-Recognition Processor and a CIS Integrated with Always-On Haar-Like Face Detector. 2017 IEEE International Solid-State Circuits Conference (ISSCC), Date of Conference: Feb. 5-9, 2017.

International Search Report and English translation thereof dated Oct. 29, 2019 in connection with International Application No. PCT/JP2019/030097.

* cited by examiner

IMAGE CAPTURING DEVICE AND VEHICLE CONTROL SYSTEM

CROSS-REFERENCE TO RELATED APPLICATIONS

This application claims the benefit under 35 U.S.C. § 371 as a U.S. National Stage Entry of International Application No. PCT/JP2019/030097, filed in the Japanese Patent Office as a Receiving Office on Jul. 31, 2019, which claims priority to Japanese Patent Application Number JP2019-140197, filed in the Japanese Patent Office on Jul. 30, 2019; Japanese Patent Application Number JP2019-139196, filed in the Japanese Patent Office on Jul. 29, 2019; and Japanese Patent Application Number JP2018-144173, filed in the Japanese Patent Office on Jul. 31, 2018, each of which is hereby incorporated by reference in its entirety.

FIELD

The present disclosure relates to an image capturing device and a vehicle control system. Specifically, the present disclosure relates to image data fabrication processing in a chip.

BACKGROUND

An image sensor including a complementary metal oxide semiconductor (CMOS) and a digital signal processor (DSP) is mounted on an instrument such as a digital camera. In the image sensor, a captured image is supplied to the DSP, provided with various processing at the DSP, and output to an external device such as an application processor.

CITATION LIST

Patent Literature

Patent Literature 1: WO 2018/051809

SUMMARY

Technical Problem

However, in the above-described conventional technology, it is typical that uncomplicated image processing such as noise removal is executed at the DSP in the image sensor whereas complicated processing such as face authentication using image data is executed at, for example, an application processor. Accordingly, an image captured by the image sensor is directly output to the application processor, and thus it is desired to execute fabrication processing in a chip of the image sensor in terms of security and privacy.

Thus, the present disclosure provides an image capturing device and a vehicle control system that are capable of executing fabrication processing in a chip of an image sensor.

Solution to Problem

To solve the above-described problem, an image capturing device according to one aspect of the present disclosure, comprises: an image capturing unit mounted on a vehicle and configured to generate image data by performing image capturing of a peripheral region of the vehicle; a scene recognition unit configured to recognize a scene of the peripheral region based on the image data; and a drive control unit configured to control drive of the image capturing unit based on the scene recognized by the scene recognition unit.

Advantageous Effects of Invention

According to the present disclosure, it is possible to execute fabrication processing in a chip of an image sensor. Note that the above-described effect is not necessarily restrictive, but any effect indicated in the present disclosure may be achieved.

BRIEF DESCRIPTION OF DRAWINGS

FIG. 13 is a diagram for description of a scene in which the own-vehicle according to the fourth embodiment travels on a straight road of a freeway, a tollway, or the like.

FIG. 14 is a diagram for description of a scene in which the own-vehicle according to the fourth embodiment travels on a curve of a freeway, a tollway, or the like.

DESCRIPTION OF EMBODIMENTS

Figure 1:
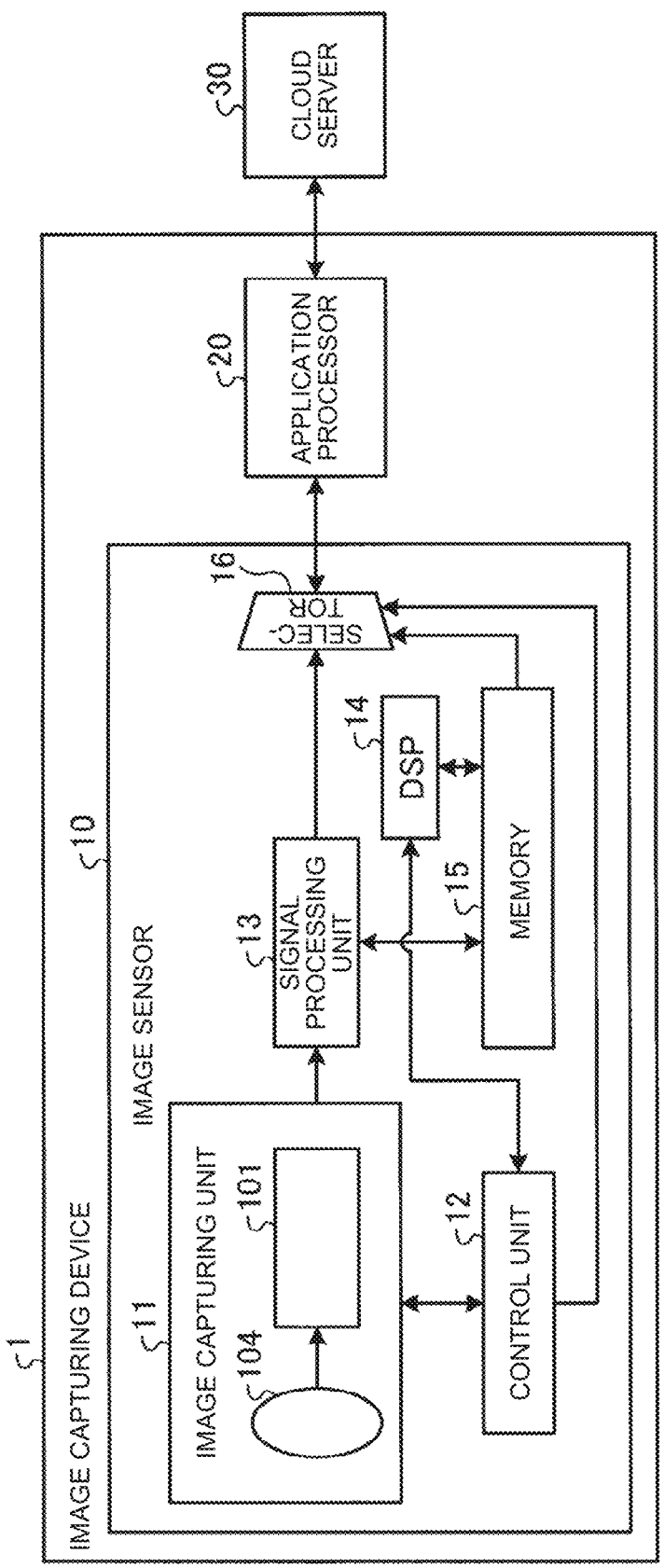
FIG. 1 is a block diagram illustrating an exemplary schematic configuration of an image capturing device as an electronic device according to a first embodiment.

Embodiments of the present disclosure will be described below in detail with reference to the accompanying drawings. Note that, in the embodiments below, any identical sites are denoted by an identical reference sign, and duplicate description thereof is omitted.

The present disclosure will be described in accordance with the order of contents described below.
1. First Embodiment
2. Modification of first embodiment
3. Second Embodiment
4. Third Embodiment
5. Fourth Embodiment
6. Chip configuration of image sensor
7. Exemplary arrangement
8. Other embodiments
9. Exemplary application to moving object
10. Exemplary application to endoscope operation system
11. Exemplary application to whole slide imaging (WSI) system 1. First Embodiment

[1-1. Configuration of Image Processing System According to First Embodiment]

FIG. 1 is a block diagram illustrating an exemplary schematic configuration of an image capturing device as an electronic device according to a first embodiment. As illustrated in FIG. 1, this image capturing device 1 is connected with a cloud server 30 to perform communication therebetween. Note that the image capturing device 1 and the cloud server 30 are connected with each other through various wired and wireless networks, a universal serial bus (USB) cable, and the like to perform communication therebetween.

The cloud server 30 is an exemplary server device configured to store image data such as still and moving images transmitted from the image capturing device 1. For example, the cloud server 30 stores the image data in arbitrary units of user, date, image capturing place, and the like and can provide various services such as album production using the image data.

The image capturing device 1 is an exemplary electronic device including an image sensor 10 and an application processor 20, and is, for example, a digital camera, a digital video camera, a tablet terminal, or a smartphone. Note that embodiments below are described by using an example in which an image is captured, but the present disclosure is not limited thereto, and a moving image or the like can be processed in a similar manner.

The image sensor 10 is, for example, a complementary metal oxide semiconductor (CMOS) image sensor constituted by one chip, receives incident light, performs photoelectric conversion, and outputs image data corresponding to the received-light quantity of the incident light to the application processor 20.

The application processor 20 is an exemplary processor such as a central processing unit (CPU) configured to execute various applications. The application processor 20 executes various kinds of processing corresponding to an application, such as display processing of displaying the image data input from the image sensor 10 on a display, biometric authentication processing using the image data, and transmission processing of transmitting the image data to the cloud server 30.

[1-2. Configuration of Image Capturing Device According to First Embodiment]

As illustrated in FIG. 1, the image capturing device 1 includes the image sensor 10 as a solid-state image capturing device, and the application processor 20. The image sensor 10 includes an image capturing unit 11, a control unit 12, a signal processing unit 13, a DSP (also referred to as processing unit) 14, a memory 15, and a selector 16 (also referred to as output unit).

The image capturing unit 11 includes an optical system 104 including a zoom lens, a focus lens, an aperture, and the like, and a pixel array unit 101 having a configuration in which unit pixels each including a light receiving element (also referred to as photoelectrical conversion unit) such as a photodiode are arrayed in a two-dimensional matrix. Light incident from the outside is imaged, through the optical system 104, onto a light-receiving surface of the pixel array unit 101, on which the light receiving elements are arrayed. Each unit pixel of the pixel array unit 101 photoelectrically converts light incident on the light receiving element and accumulates electric charge in accordance with the light quantity of the incident light in a readable manner.

The image capturing unit 11 also includes a converter (analog-to-digital converter; hereinafter referred to as ADC) 17 (refer to FIG. 2, for example). The ADC 17 generates digital image data by converting an analog pixel signal read from the image capturing unit 11 for each unit pixel into a digital value, and outputs the generated image data to the signal processing unit 13. Note that the ADC 17 may include, for example, a voltage generation circuit configured to generate drive voltage for driving the image capturing unit 11 from power voltage or the like.

The size of image data output from the image capturing unit 11 may be selected from among a plurality of sizes such as 12 M (3968×2976) pixels and a Video Graphics Array (VGA) size (640×480 pixels Z). In addition, for example, it is possible to select whether a color image of RGB (red, green, and blue) or a grayscale image with luminance only is to be generated from the image data output from the image capturing unit 11. Each selection may be performed as a kind of setting of an image capturing mode.

The control unit 12 controls each component in the image sensor 10 in accordance with, for example, a user operation and a set operation mode.

The signal processing unit 13 executes various kinds of signal processing on digital image data read from the image capturing unit 11 or digital image data read from the memory 15 (hereinafter referred to as processing target image data). For example, when the processing target image data is a color image, the signal processing unit 13 performs format conversion of the image data into YUV image data, RGB image data, or the like. The signal processing unit 13 also executes processing such as noise removal or white balance adjustment on the processing target image data as necessary. In addition, the signal processing unit 13 executes, on the processing target image data, various kinds of signal processing (also referred to as preprocessing) needed for the DSP 14 to process the image data.

The DSP 14 executes, for example, a computer program stored in the memory 15 to function as a processing unit configured to execute various kinds of processing by using a learning-completed model produced by machine learning using a deep neural network (DNN). For example, the DSP 14 executes arithmetic processing based on a learning-completed model stored in the memory 15 to execute processing of multiplying image data by a dictionary coefficient stored in the memory 15. A result (calculation result) obtained through such arithmetic processing is output to the memory 15 and/or the selector 16. Note that the calculation result may include image data obtained by executing arithmetic processing using a learning-completed model, and various kinds of information (metadata) obtained from the image data. In addition, a memory controller configured to control access to the memory 15 may be incorporated in the DSP 14.

Some types of arithmetic processing use, for example, a learning-completed learning model as an exemplary neural network calculation model. For example, the DSP 14 can execute DSP processing as various kinds of processing by using the learning-completed learning model. For example, the DSP 14 reads image data from the memory 15, inputs the image data into the learning-completed learning model, and acquires, as a result output from the learning-completed model, a face position such as a face outline or a region of a face image. Then, the DSP 14 generates fabricated image data by executing processing such as masking, mosaicing, or avatar creation on an extracted face position in the image data. Thereafter, the DSP 14 stores the generated fabricated image data in the memory 15.

The learning-completed learning model includes a DNN, a support vector machine, or the like having learned, for example, detection of the face position of a person by using learning data. Having received image data as determination target data, the learning-completed learning model outputs region information such as an address that specifies a determination result, in other words, a face position. Note that the DSP 14 may update a learning model by changing weights of various parameters in the learning model by using learning data, may prepare a plurality of learning models and change a learning model to be used in accordance with the contents of arithmetic processing, or may acquire or update a learning-completed learning model from an external device, thereby executing the above-described arithmetic processing.

Note that image data as a processing target of the DSP 14 may be image data normally read from the pixel array unit 101 or may be image data having a data size reduced by thinning pixels of the normally read image data. Alternatively, the image data may be image data read in a data size smaller than normal by executing thinned-pixel reading from the pixel array unit 101. Note that the normal reading may be reading without pixel thinning.

Through such face position extraction and fabrication processing by using a learning model, it is possible to generate fabricated image data provided with masking at a face position of image data, fabricated image data provided with mosaic processing at a face position of image data, or fabricated image data provided with avatar creation by placing a character at a face position of image data.

The memory 15 stores image data output from the image capturing unit 11, image data provided with signal processing by the signal processing unit 13, the calculation result obtained at the DSP 14, and the like as necessary. The memory 15 also stores, as a computer program and a dictionary coefficient, an algorithm of a learning-completed learning model, which is executed by the DSP 14.

In addition to image data output from the signal processing unit 13 and image data (hereinafter referred to as fabricated image data) provided with arithmetic processing and output from the DSP 14, the memory 15 may store an ISO (International Organization for Standardization) sensitivity, an exposure time, a frame rate, a focus, an image capturing mode, a clipping range, and the like. Thus, the memory 15 may store various kinds of image capturing information set by a user.

The selector 16 selectively outputs fabricated image data output from the DSP 14 or image data stored in the memory 15 in accordance with, for example, a selection control signal from the control unit 12. For example, the selector 16 selects, based on setting by the user or the like, any of calculation results such as fabricated image data and metadata stored in the memory 15, and outputs the selected calculation result to the application processor 20.

For example, when a fabrication processing mode in which fabricated image data is output is selected, the selector 16 reads fabricated image data generated by the DSP 14 from the memory 15 and outputs the fabricated image data to the application processor. When a normal processing mode in which fabricated image data is not output is selected, the selector 16 outputs, to the application processor, image data input from the signal processing unit 13. Note that, when a first processing mode is selected, the selector 16 may directly output, to the application processor 20, a calculation result output from the DSP 14.

The image data and the fabricated image data output from the selector 16 as described above are input to the application processor 20 configured to process display, a user interface, and the like. The application processor 20 is achieved by, for example, a CPU or the like and executes an operating system, various kinds of application software, and the like. The application processor 20 may have functions of a graphics processing unit (GPU), a baseband processor, and the like. The application processor 20 executes various kinds of processing on input image data and calculation result as needed, executes display to the user, and executes transmission to the external cloud server 30 through a predetermined network 40.

Note that various kinds of networks such as the Internet, a wired local area network (LAN), a wireless LAN, a mobile communication network, and Bluetooth (registered trademark) may be applied as the predetermined network 40. The transmission destination of image data and a calculation result is not limited to the cloud server 30 but may be various kinds of information processing devices (systems) having a communication function, for example, a stand-alone server, a file server configured to store various kinds of data, and a communication terminal such as a cellular phone.

[1-3. Description of Image Fabrication According to First Embodiment]

Figure 2:
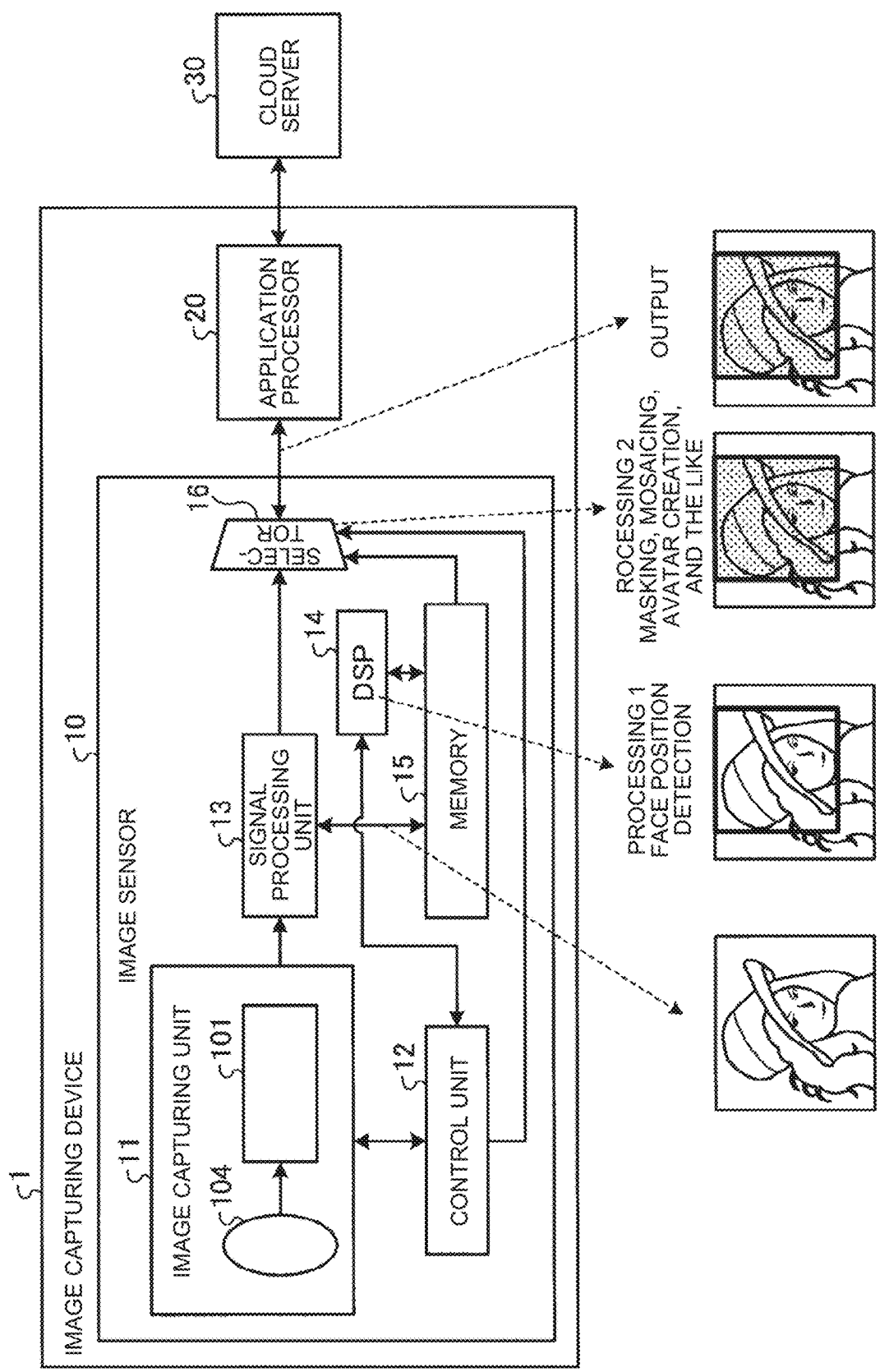
FIG. 2 is a diagram for description of fabrication image according to the first embodiment.

FIG. 2 is a diagram for description of image fabrication according to the first embodiment. As illustrated in FIG. 2, the signal processing unit 13 performs signal processing on image data read from the image capturing unit 11 and stores the image data in the memory 15. The DSP 14 reads the image data from the memory 15 and detects a face position from the image data by executing face detection using a learning-completed learning model (Processing 1).

Subsequently, the DSP 14 generates fabricated image data by executing the fabrication processing (Processing 2) of providing masking, mosaicing, and the like on the detected face position and stores the fabricated image data in the memory 15. Thereafter, the selector 16 outputs the fabricated image data in which a face region is fabricated in accordance with selection by the user to the application processor 20.

[1-4. Process of Processing According to First Embodiment]

Figure 3:
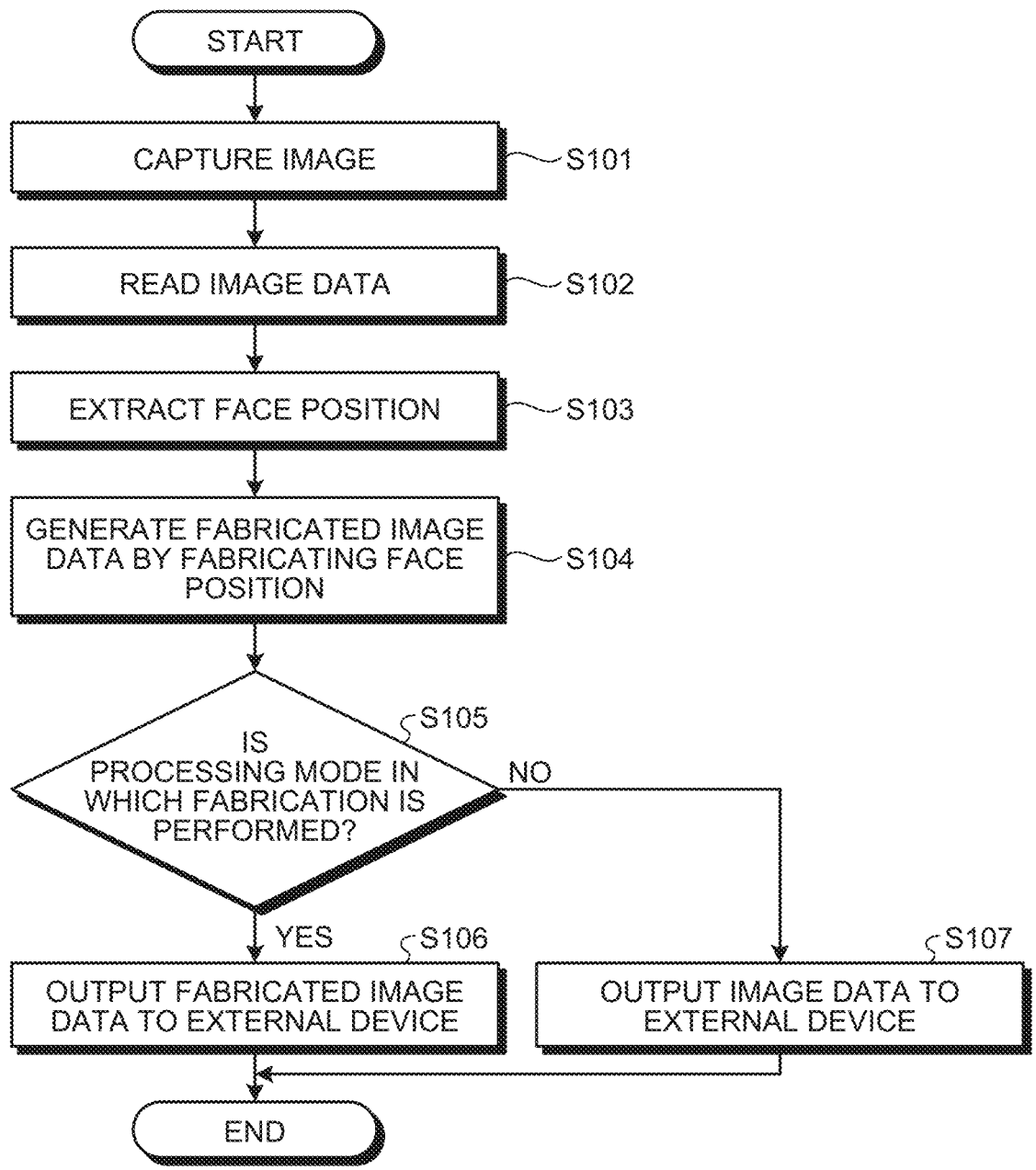
FIG. 3 is a flowchart illustrating the process of fabrication processing according to the first embodiment.

FIG. 3 is a flowchart illustrating the process of the fabrication processing according to the first embodiment. As illustrated in FIG. 3, image data captured by the image capturing unit 11 is stored in the memory 15 (S101).

Then, the DSP 14 reads the image data from the memory 15 (S102) and detects a face position by using a learning-completed learning model (S103). Subsequently, the DSP 14 generates fabricated image data by fabricating the image data at the face position and stores the fabricated image data in the memory 15 (S104).

Thereafter, when the fabrication processing mode as a processing mode in which fabrication is performed is selected (Yes at S105), the selector 16 reads the fabricated image data from the memory 15 and outputs the fabricated image data to an external device such as the application processor 20 (S106).

When the normal processing mode as a processing mode in which no fabrication is performed is selected (No at S105), the selector 16 reads the image data not provided with the fabrication processing from the memory 15 and outputs the image data to an external device such as the application processor 20 (S107).

[1-5. Effects]

As described above, the image sensor 10 can execute the fabrication processing in a closed region in one chip when fabrication is necessary, it is possible to prevent captured image data from being directly output to the outside, thereby achieving security improvement and privacy protection. In addition, the image sensor 10 allows the user to select whether to execute fabrication, and thus a processing mode can be selected in accordance with usage to improve convenience of the user.

2. Modification of the First Embodiment

The first embodiment describes above an example in which masking and the like are executed at a face position, but the fabrication processing is not limited thereto. For example, a partial image to which a face position is extracted may be generated.

Figure 4:
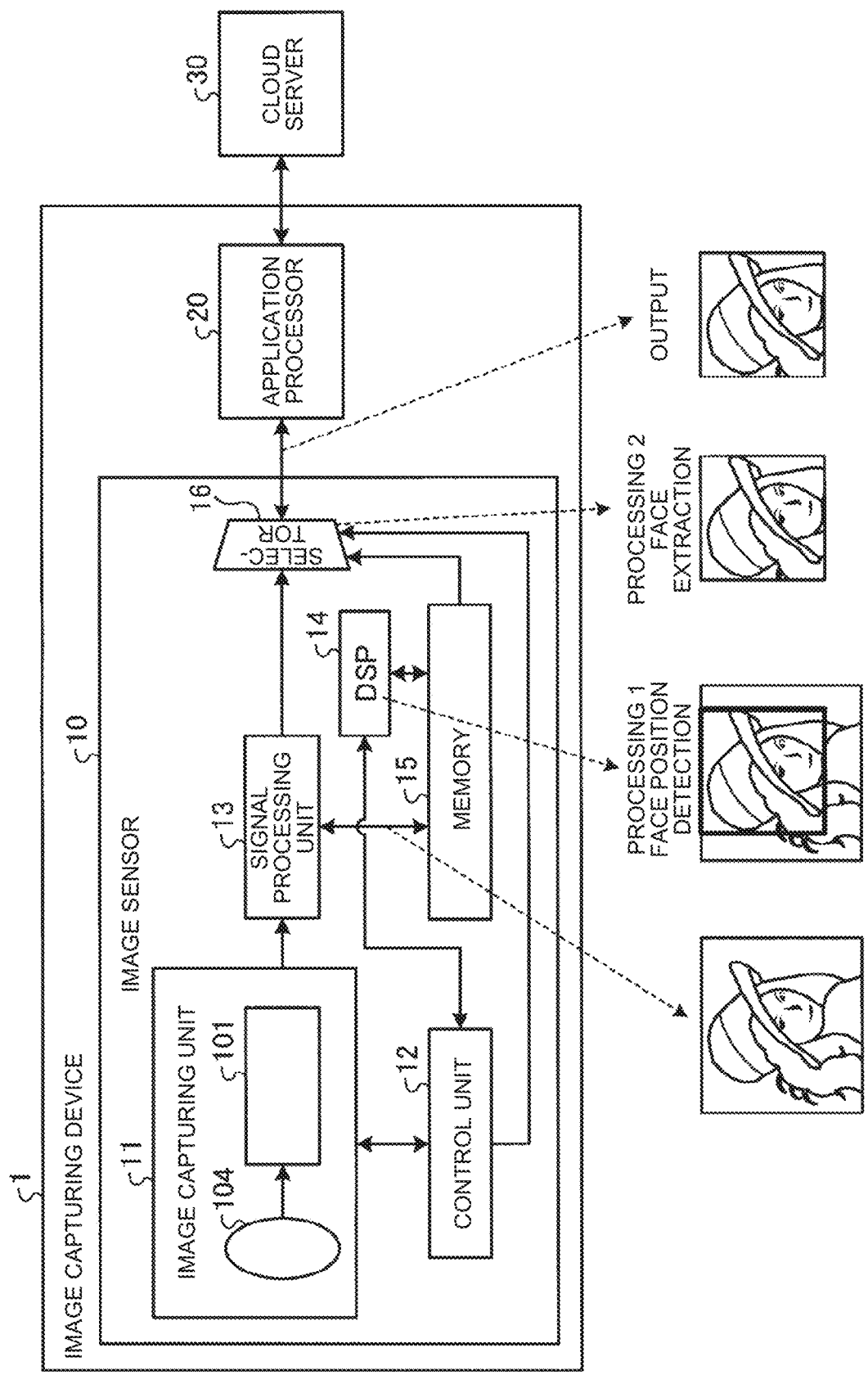
FIG. 4 is a diagram for description of a modification of the first embodiment.

FIG. 4 is a diagram for description of a modification of the first embodiment. As illustrated in FIG. 4, the signal processing unit 13 performs signal processing on image data read from the image capturing unit 11 and stores the image data in the memory 15. The DSP 14 reads the image data from the memory 15 and detects a face position from the image data by executing face detection using a learning-completed learning model (Processing 1).

Subsequently, the DSP 14 generates a partial image data to which the detected face position is extracted (Processing 2), and stores the partial image data in the memory 15. Thereafter, the selector 16 outputs partial image data of the face in accordance with selection of the user to the application processor 20.

As described above, the image sensor 10 can execute extraction of partial image data in a closed region in one chip when fabrication is necessary, and thus can output an image in accordance with processing of the application processor 20, such as person specification, face authentication, or image collection for each person. As a result, it is possible to prevent transmission of an unnecessary image, thereby achieving security improvement and privacy protection as well as data volume reduction.

3. Second Embodiment

[3-1. Description of Image Capturing Device According to Second Embodiment]

Although the first embodiment describes an example in which the DSP 14 executes the fabrication processing, the present disclosure is not limited thereto, and the selector 16 may perform the fabrication processing. Thus, a second embodiment describes an example in which the selector 16 performs the fabrication processing.

Figure 5:
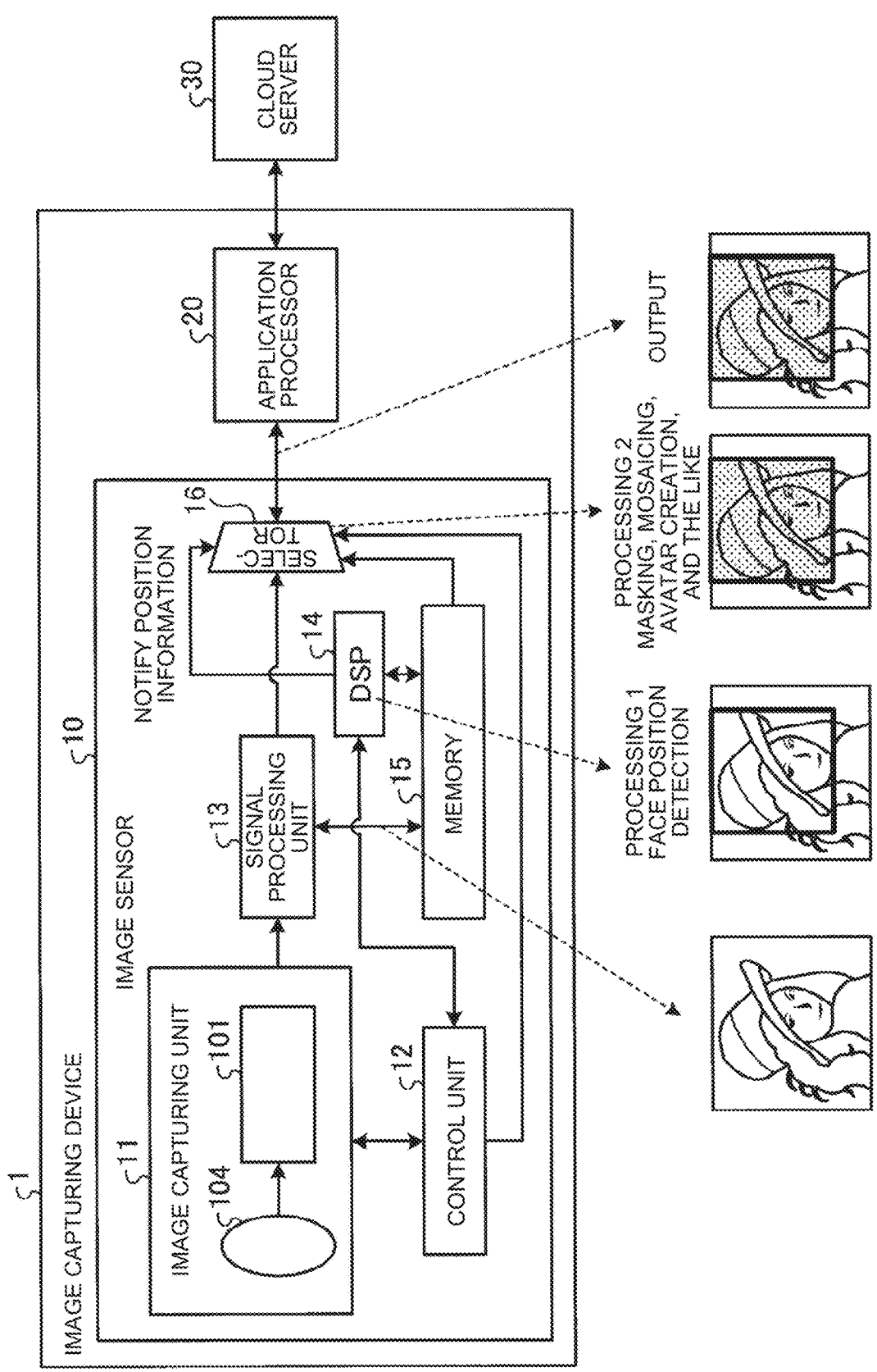
FIG. 5 is a diagram for description of the image capturing device according to a second embodiment.

FIG. 5 is a diagram for description of an image capturing device according to the second embodiment. As illustrated in FIG. 5, the configuration of the image sensor 10 according to the second embodiment is same as that of the image sensor 10 according to the first embodiment, and thus detailed description thereof is omitted. Difference from the first embodiment is that the DSP 14 of the image sensor 10 notifies the selector 16 of position information of a face position extracted by using a learning model.

For example, as illustrated in FIG. 5, the signal processing unit 13 performs signal processing on image data read from the image capturing unit 11 and stores the image data in the memory 15. The DSP 14 reads the image data from the memory 15 and detects a face position from the image data by executing face detection using a learning-completed learning model (Processing 1). Then, the DSP 14 notifies the selector 16 of position information such as an address that specifies the face position.

When the fabrication processing is selected by the user, the selector 16 reads image data from the memory 15 and specifies a region of interest (ROI) as a fabrication target by using the position information acquired from the DSP 14. Then, the selector 16 generates fabricated image data by executing the fabrication processing such as masking on the specified ROI (Processing 2) and outputs the fabricated image data to the application processor 20. Note that the selector 16 stores the fabricated image data in the memory 15.

[3-2. First Modification of Second Embodiment]

Similarly to the above-described modification of the first embodiment, in the second embodiment as well, the selector 16 may generate a partial image to which a face position is extracted.

Figure 6:
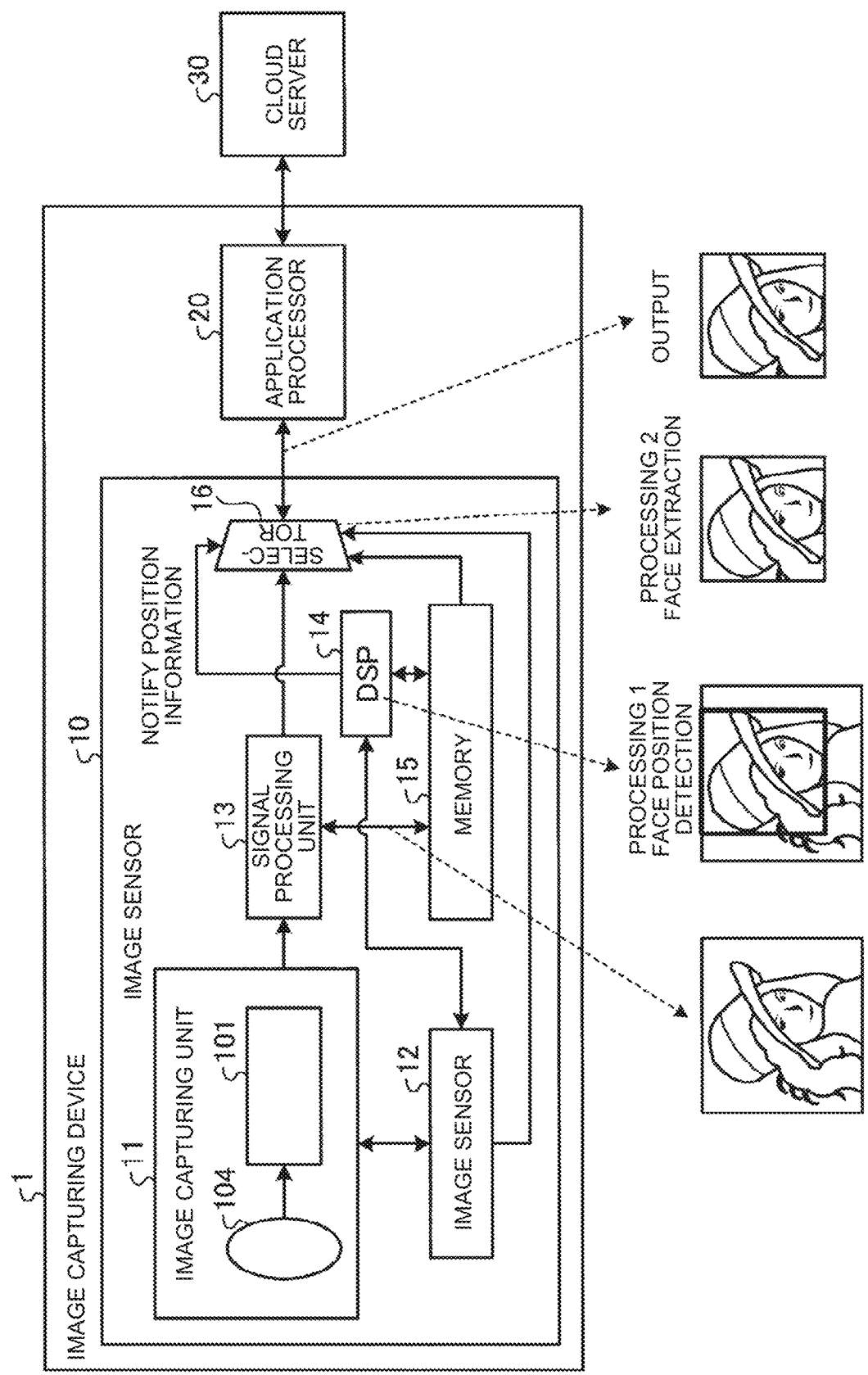
FIG. 6 is a diagram for description of a modification of the second embodiment.

FIG. 6 is a diagram for description of a first modification of the second embodiment. As illustrated in FIG. 6, the signal processing unit 13 performs signal processing on image data read from the image capturing unit 11 and stores the image data in the memory 15. The DSP 14 reads the image data from the memory 15 and detects a face position from the image data by executing face detection using a learning-completed learning model (Processing 1). Then, the DSP 14 notifies the selector 16 of position information such as an address that specifies the face position.

Subsequently, when the fabrication processing is selected by the user, the selector 16 reads the image data from the memory 15 and specifies a region of interest (ROI) as a fabrication target by using the position information acquired from the DSP 14. Thereafter, the selector 16 generates partial image data to which a part corresponding to the ROI is extracted from the image data (Processing 2), and outputs the partial image data to the application processor 20.

[3-3. Second Modification of Second Embodiment]

Although the second embodiment and the first modification thereof describe above an example case in which the selector 16 performs Processing 2 such as ROI extraction (also referred to as clipping or trimming) and fabrication (for example, masking) on image data stored in the memory 15, the present disclosure is not limited thereto, and for example, the selector 16 may directly execute Processing 2 such as ROI clipping and fabrication (for example, masking) on image data output from the signal processing unit 13.

[3-4. Third Modification of Second Embodiment]

Image data read from the image capturing unit 11 may be partial image data of an ROI only or image data including no ROI. In this case, the control unit 12 is notified of a face position extracted from a first frame by the DSP 14 and executes, for the image capturing unit 11, reading of partial image data from a pixel region corresponding to an ROI in a second frame as the next frame of the first frame, and reading of image data from a pixel region corresponding to a region other than the ROI.

Note that in the second embodiment and the modification thereof, the selector 16 is not limited to the fabrication processing such as masking but may rewrite a region corresponding to an ROI in image data into another image and output the image or may read regions except for a region corresponding to an ROI in image data from the memory 15 and output the regions. Note that this processing may be executed by the DSP 14 in the first embodiment.

Since the image sensor 10 can execute the fabrication processing at the selector 16 as described above, it is possible to reduce a processing load on the DSP 14 when the fabrication processing is unnecessary. In addition, since the image sensor 10 can output an image fabricated at the selector 16 without storing the image in the memory 15, it is possible to reduce the used volume of the memory 15, thereby achieving cost and size reduction of the memory 15. As a result, the size of the entire image sensor 10 can be reduced.

4. Third Embodiment

[4-1. Description of Image Capturing Device According to Third Embodiment]

The image sensor 10 can increase the processing speed by reading small-volume image data before reading the entire image data from the image capturing unit 11 and by detecting a face position. Thus, a third embodiment describes an example in which the processing speed is increased.

Figure 7:
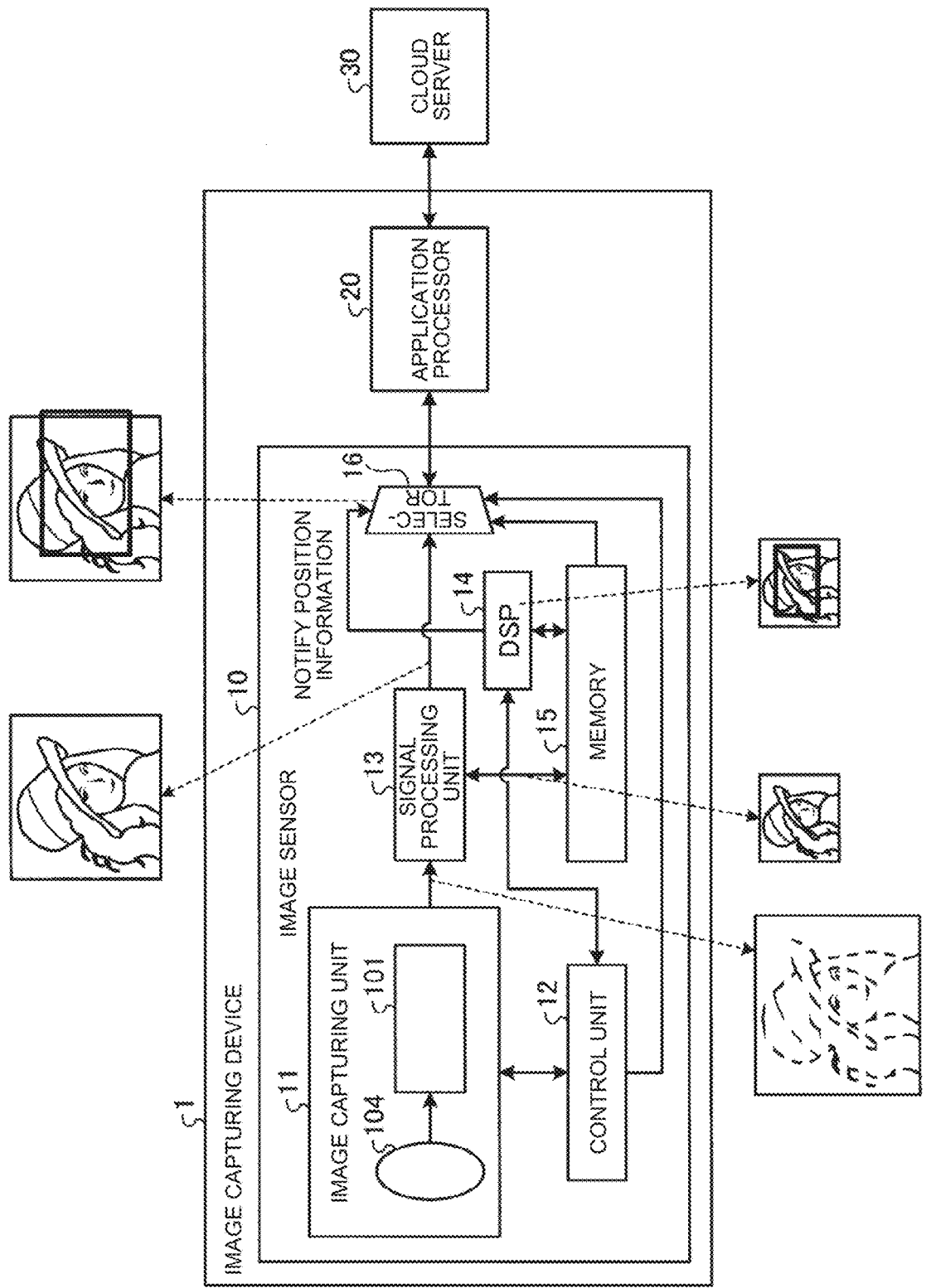
FIG. 7 is a diagram for description of the image capturing device according to a third embodiment.

FIG. 7 is a diagram for description of an image capturing device according to the third embodiment. As illustrated in FIG. 7, the configuration of the image sensor 10 according to the third embodiment is same as that of the image sensor 10 according to the first embodiment, and thus detailed description thereof is omitted. Difference from the first embodiment will be described below.

For example, as illustrated in FIG. 7, when reading image data from all unit pixels, the image capturing unit 11 performs reading from not all unit pixels but thinned target unit pixels and stores thinned small-volume image data in the memory 15. Simultaneously, the image capturing unit 11 executes normal reading of image data.

Then, the DSP 14 reads the small-volume image data from the memory 15 and detects a face position from the image data by executing face detection using a learning-completed learning model (Processing 1). Then, the DSP 14 notifies the selector 16 of position information such as an address that specifies the face position.

Thereafter, when having received the normal image data read by the image capturing unit 11, the selector 16 specifies a region of interest (ROI) as a fabrication target from the normal image data by using the position information acquired from the DSP 14. Then, the selector 16 generates fabricated image data by executing the fabrication processing such as masking in a region corresponding to the ROI (Processing 2) and outputs the fabricated image data to the application processor 20.

[4-2. Process of Processing According to Third Embodiment]

Figure 8:
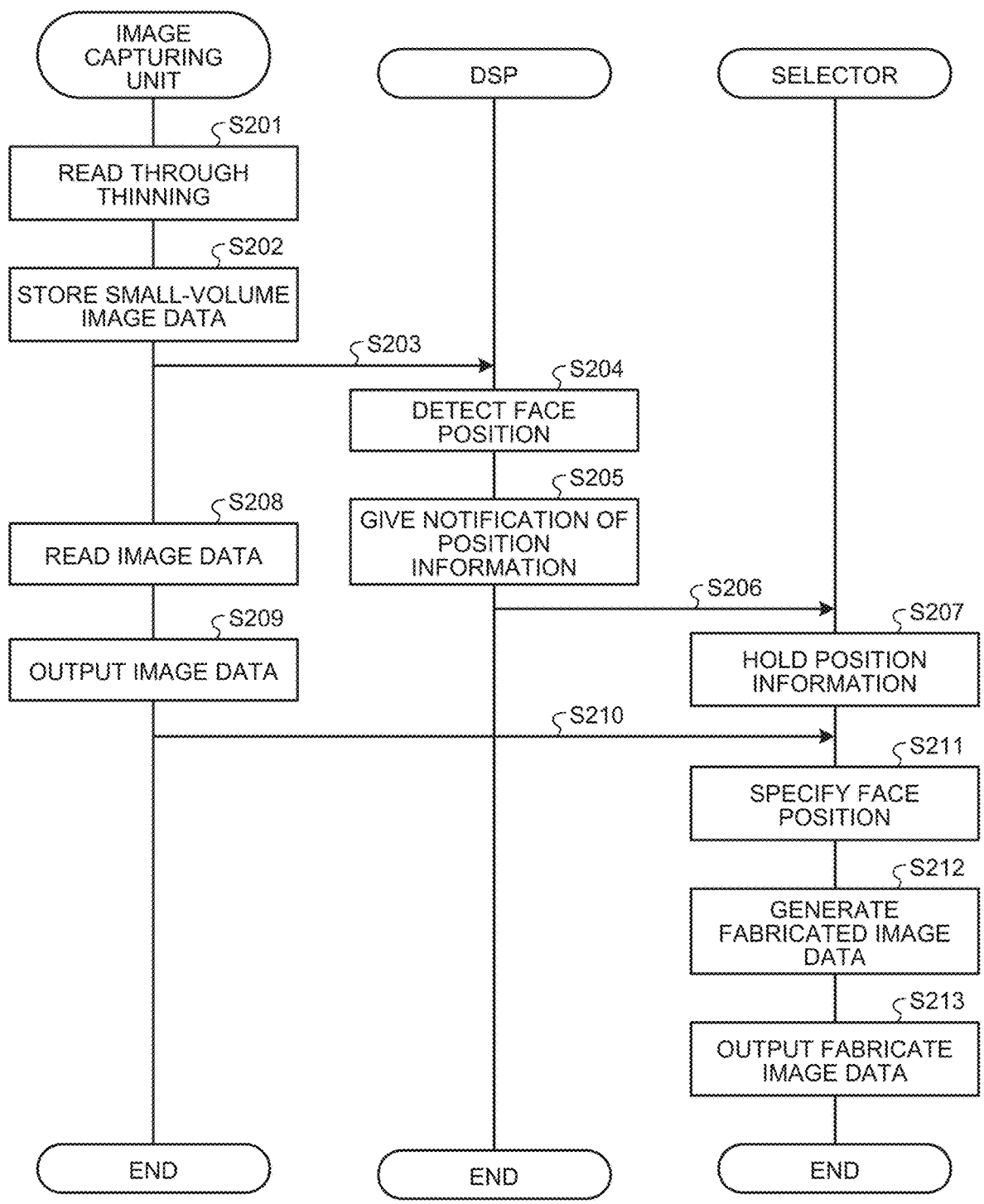
FIG. 8 is a sequence diagram illustrating the process of fabrication processing according to the third embodiment.

The following describes the process of the processing described with reference to FIG. 7. FIG. 8 is a sequence diagram illustrating the process of the fabrication processing according to the third embodiment. As illustrated in FIG. 8, the image capturing unit 11 reads an image through thinning (S201) and stores thinned small-volume image data in the memory 15 (S202). Thereafter, the image capturing unit 11 reads normal image data.

Simultaneously, the DSP 14 detects a face position by executing face detection on the small-volume image data by using a DNN or the like (S203). Then, the DSP 14 notifies the selector 16 of position information of the detected face position (S205 and S206).

Then, the selector 16 holds the position information of the face position, notification of which is given by the DSP 14 (S207). Thereafter, when the reading of the normal image data is completed, the image capturing unit 11 outputs the normal image data to the selector 16 (S209 and S210), and the selector 16 specifies a face position from the normal image data by using the position information of the face position (S211).

Thereafter, the selector 16 generates fabricated image data by fabricating the face position (S212) and outputs the fabricated image data to an external device (S213). For example, the selector 16 clips and outputs only the face position detected by the DNN. In this manner, the image sensor 10 can detect the face position before the reading of the normal image data is completed, and thus can execute the fabrication processing without delay after the image data reading, and the processing speed can be increased as compared to the first embodiment.

5. Fourth Embodiment

The following describes a specific example in which the image capturing device 1 according to the above-described embodiment is applied to an on-board camera mounted on a vehicle and configured to perform image capturing of a peripheral region of the vehicle.

[5-1. Exemplary System Configuration]

Figure 9:
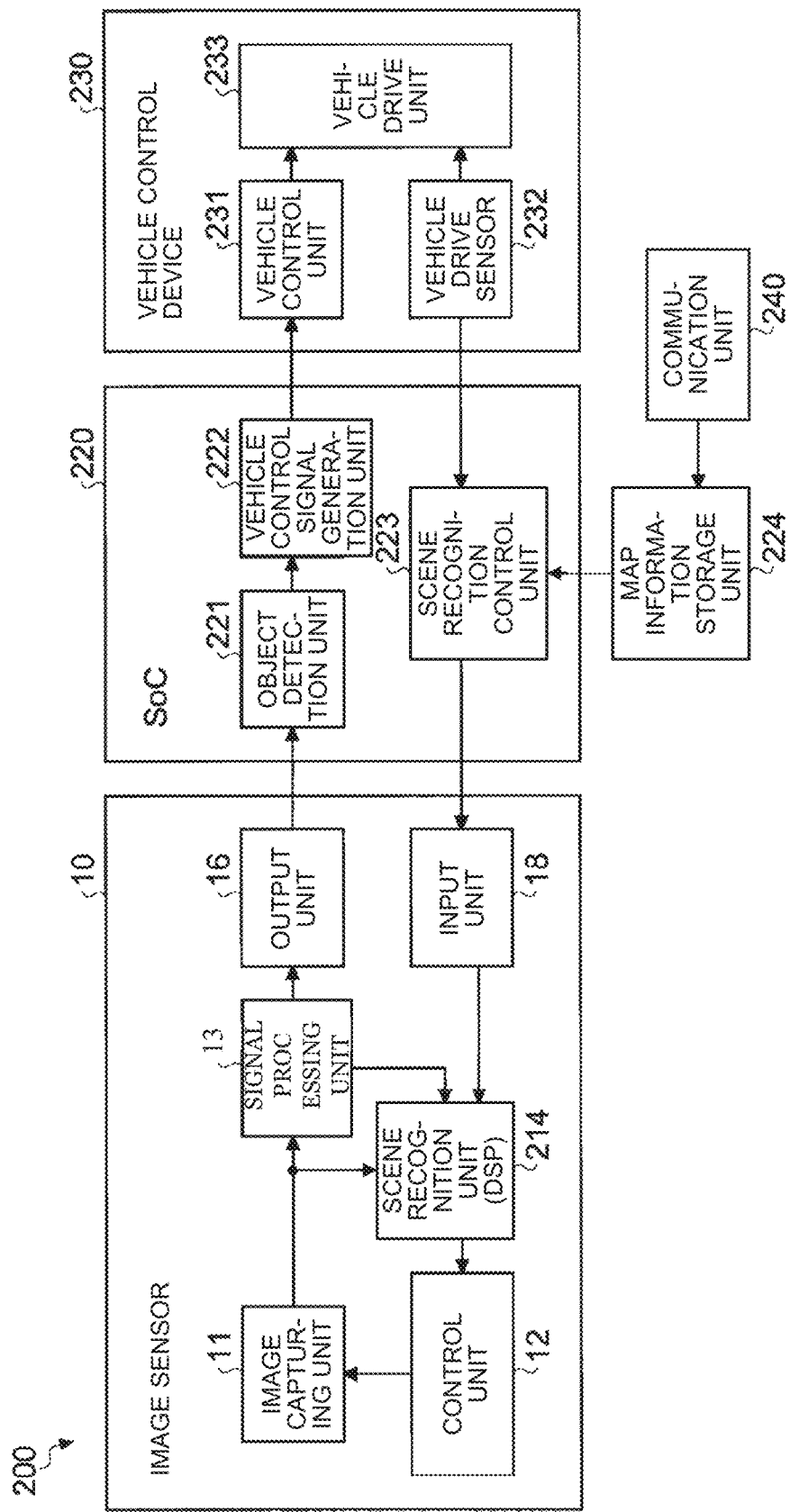
FIG. 9 is a block diagram illustrating an exemplary schematic configuration of an on-board image capturing system according to a fourth embodiment.

FIG. 9 is a block diagram illustrating an exemplary schematic configuration of an on-board image capturing system according to a fourth embodiment. As illustrated in FIG. 9, this on-board image capturing system 200 includes an image sensor 210, a system on chip (SoC) 220, and a vehicle control device 230.

(Image Sensor 10)

The image sensor 10 may be same as the image sensor 10 according to the above-described embodiment. Note that in the present embodiment, an input unit 18, description of which is omitted in the above-described embodiment, will be described, and the selector 16 is referred to as an output unit 16. In the present embodiment, the DSP 14 functions as a scene recognition unit 214 configured to recognize a scene based on input image data. In this recognition processing, a learning-completed model may be used as in the above-described embodiment.

(SoC 220)

The SoC 220 is, for example, a circuit board on which the application processor 20 or the like is mounted, and includes an object detection unit 221, a vehicle control signal generation unit 222, and a scene recognition control unit 223. For example, some or all of these units may be achieved by the application processor 20 executing a predetermined computer program or may be achieved by a dedicated chip or the like designed to execute processing of each unit.

(Vehicle Control Device 230)

The vehicle control device 230 may be, for example, an engine control unit (ECU) mounted on a vehicle, and includes a vehicle control unit 231, a vehicle drive sensor 232, and a vehicle drive unit 233.

(Map Information Storage Unit 224)

A map information storage unit 224 may be, for example, a storage unit configured to store map information such as a land shape, a traffic network, and a road width. For example, when a navigation system is mounted on the vehicle, the map information storage unit 224 may be shared with the navigation system.

(Communication Unit 240)

A communication unit 240 may be, for example, a unit configured to establish communication with a server or the like (not illustrated) through a predetermined network. The predetermined network may be various kinds of networks such as a wide area network (WAN) (including the Internet), a local area network (LAN), a public network, and a mobile communication network.

Note that the SoC 220 and the vehicle control device 230 may be connected with each other through a communication network such as a controller area network (CAN). The image sensor 10 and the SoC 220 may be connected with each other through an interface such as an inter-integrated circuit (I2C), a low voltage differential signaling (LVDS), or a mobile industry processor interface (MIPI).

The following describes operation of each unit in the above-described configuration.

—Object Detection Unit 221

The object detection unit 221 detects an object in surroundings of the vehicle based on, for example, calculation results of image data output from the image sensor 10, fabricated image data based on the image data, metadata, and the like.

—Vehicle Control Signal Generation Unit 222

The vehicle control signal generation unit 222 generates a vehicle control signal for controlling acceleration, deceleration, steering, or the like of the vehicle based on an object detection result output from the object detection unit 221.

—Vehicle Drive Unit 233

The vehicle drive unit 233 may be, for example, an engine system, a transmission system, a brake system, an air-bag device, a display system such as an instrument panel, an acoustic system, or an air-conditioning system of the vehicle.

—Vehicle Drive Sensor 232

The vehicle drive sensor 232 may be various sensors for detecting the drive state of an engine, a drive motor, or the like, detecting the steering angle, and detecting the brake operation state.

Vehicle Control Unit 231

The vehicle control unit 231 is configured as, for example, a central processing unit (CPU), and controls the vehicle drive unit 233 based on a vehicle control signal based on a drive operation by a driver, and a vehicle control signal input from the vehicle control signal generation unit 222 of the SoC 220.

Scene Recognition Control Unit 223

The scene recognition control unit 223 specifies information such as a place currently traveled by the vehicle, the land shape (such as slope or curve) thereof, the traveling speed, and the status of acceleration and deceleration based on a detection result input from the vehicle drive sensor 232 and map information read from the map information storage unit 224, and generates, based on the specified information, a control signal for controlling the scene recognition unit 214. The generated control signal is input to the scene recognition unit 214 through the input unit 18.

Scene Recognition Unit 214

The scene recognition unit 214 is the DSP 14 of the image sensor 10 as described above, and recognizes the current scene based on image data read from the image capturing unit 11 (or image data obtained by thinning the read image data) and a control signal input from the scene recognition control unit 223. Note that a scene in the present description is not limited to a scene specified based on a background, an object, and the like in the view angle of the image capturing unit 11, but may be include the posture (such as tilt with respect to the horizontal direction), the traveling speed, the status of acceleration and deceleration, the status of turning (such as right turn or left turn), and the like of the vehicle. Although illustration of the memory 15 is omitted in FIG. 9, calculation results such as fabricated image data and metadata stored in the memory 15 may be input to the scene recognition unit 214.

Control Unit 12

The control unit 12 is a drive control unit configured to drive the pixel array unit 101 and switches drive when image data is read from the image capturing unit 11 based on a scene recognized by a scene recognition unit 215.

[5-2. Exemplary Operation]

Figure 10:
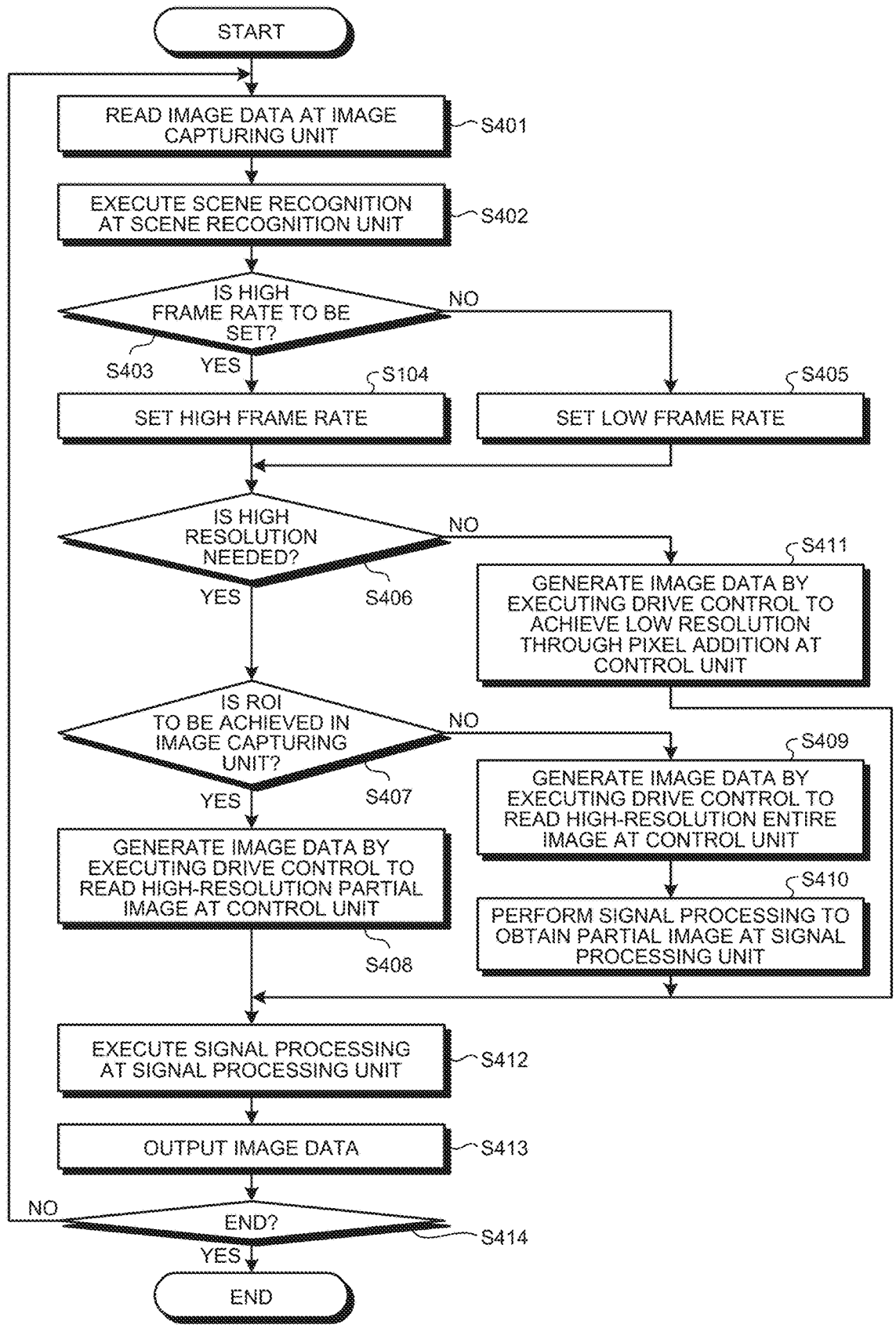
FIG. 10 is a flowchart illustrating an exemplary operation process according to the fourth embodiment.

The following describes an operation process according to the present embodiment in detail with reference to the accompanying drawings. FIG. 10 is a flowchart illustrating an exemplary operation process according to the present embodiment.

As illustrated in FIG. 10, in the present embodiment, first, reading of image data is executed at the image capturing unit 11 (step S401). The read image data may be image data normally read from the pixel array unit 101 or may be image data having a data size reduced by thinning pixels in the normally read image data. Alternatively, the read image data may be image data read in a data size smaller than normal by executing reading with thinned pixels from the pixel array unit 101.

Subsequently, scene recognition is executed at the scene recognition unit 214 (step S402). Specifically, the scene recognition unit 214 recognizes the current scene based on image data input from the image capturing unit 11 or the signal processing unit 13 (or the memory 15) and a control signal input from the scene recognition control unit 223 through the input unit 18. In the recognition, a learning-completed model may be used.

Subsequently, the scene recognition unit 214 determines, based on a result of the scene recognition, whether to set a high frame rate when image data is read from the image capturing unit 11 (step S403). The scene recognition unit 214 may determine that the frame rate is set to be high in a scene in which the situation around the vehicle changes in a relatively short duration, for example, at an intersection or fast traveling.

When the frame rate is set to be high (YES at step S403), the scene recognition unit 214 sets a high frame rate to reading from the image capturing unit 11 (step S404) and proceeds to step S406. When the frame rate is not set to be high (NO at step S403), the scene recognition unit 214 sets a low frame rate (or normal frame rate) to reading from the image capturing unit 11 (step S405) and proceeds to step S406.

Note that the high frame rate may be, for example, 30 frames per second (fps), and the low frame rate (or normal frame rate) may be, for example, a frame rate (for example, 10 fps) lower than the high frame rate. However, these specific values are merely exemplary and may be changed to various values.

Subsequently, the scene recognition unit 214 determines whether high-resolution image data is needed (step S406). For example, in a case in which the traveling speed is higher than a certain speed or in a scene, such as a freeway or a tollway, in which the moving speeds of other vehicles and the like are relatively fast, the scene recognition unit 214 may determine that high-resolution image data is needed to detect a far object.

When determining that high-resolution image data is needed (YES at step S406), the scene recognition unit 214 determines whether extraction of image data of a region of interest (ROI) is to be achieved in the image capturing unit 11, in other words, whether image data of the ROI only is to be read from the image capturing unit 11 or image data of the ROI is to be cut out of image data read from the image capturing unit 11 (step S407). When the scene recognition unit 214 determines that extraction of image data of the ROI is to be achieved in the image capturing unit 11 (YES at step S407), the control unit 12 generates image data by executing drive control on the image capturing unit 11 to read image data of the ROI at high resolution (step S408) and proceeds to step S412. When the scene recognition unit 214 determines that extraction of image data of the ROI is not to be achieved in the image capturing unit 11 (NO at step S407), the control unit 12 generates image data by executing drive control on the image capturing unit 11 to read image data of the entire image at high resolution (step S409). Subsequently, the read image data of the entire image is input to the signal processing unit 13, partial image data of the ROI is cut out of the entire image at the signal processing unit 13 (step S410), and thereafter, the process proceeds to step S412.

When the scene recognition unit 214 determines that high-resolution image data is not needed at step S406 (NO at step S406), the control unit 12 generates image data by executing drive control on the image capturing unit 11 to read image data of the entire image at low resolution (step S411) and proceeds to step S412. Note that, for example, readout drive that reduces the resolution by adding the pixel values of adjacent pixels or readout drive that reduces the resolution by skipping (thinning) pixels may be executed in the low-resolution readout operation.

Note that, at step S406, the scene recognition unit 214 may calculate the illuminance of the vehicle peripheral region based on image data and determine whether image data is to be read at low resolution or high resolution based on the calculated illuminance. For example, in a case in which it is determined that a far object needs to be detected, the scene recognition unit 214 may determine that image data is to be read at low resolution when the illuminance is lower than a predetermined threshold.

At step S412, the signal processing unit 13 executes predetermined signal processing on the input image data of the entire image or partial image. The predetermined signal processing is, for example, gain adjustment, white balance adjustment, black level correction, dynamic range adjustment, or defect pixel correction. Then, the image data provided with the signal processing is output to, for example, the object detection unit 221 through the output unit 16 (step S413).

Thereafter, it is determined whether the present operation is to be ended based on, for example, an instruction input from the outside and vehicle power information (step S414), and the present operation returns to step S401 when the present operation is to be continued (NO at step S414). When the present operation is to be ended (YES at step S414), the present operation is ended.

[5-3. Specific Exemplary Operations]

Subsequently, specific examples of the operation described with reference to FIG. 10 will be described below with some exemplary scenes.

[5-3-1. Scene of Intersection]

Figure 11:
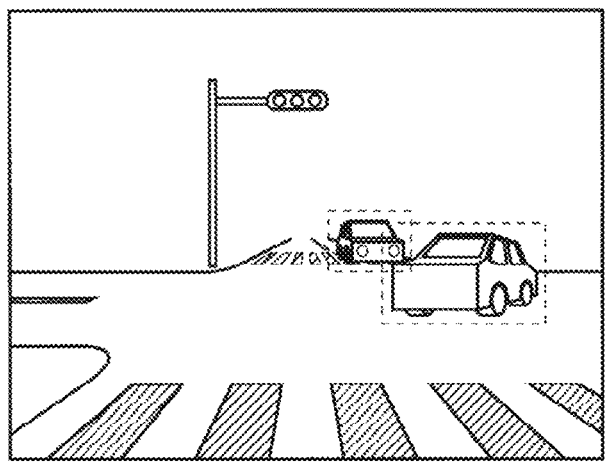
FIG. 11 is a diagram for description of a scene in which an own-vehicle according to the fourth embodiment enters an intersection.

FIG. 11 is a diagram for description of a scene in which the own-vehicle enters an intersection. As illustrated in FIG. 11, when the own-vehicle enters an intersection, the road shape of the intersection, crosswalks, traffic lights, other vehicles, pedestrians, bicycles, and the like are included in the view angle of the image capturing unit 11. In such a scene, the scene recognition unit 214 may determine that the frame rate is set to be high at step S403 in FIG. 10 (YES at step S403) to achieve vehicle control compatible with the surrounding situation that changes in a short time.

Note that since it is unlikely that a far object needs to be detected in this scene, the scene recognition unit 214 may determine that high-resolution image data is not needed at step S406 in FIG. 10 (NO at step S406). However, the present disclosure is not limited thereto, and the scene recognition unit 214 may determine that high-resolution image data is needed (YES at step S406).

In addition, since it is desirable to have a detection target range that is wide as possible to detect a suddenly crossing pedestrian or the like in the scene, the scene recognition unit 214 may set the ROI to be the entire view angle of the image capturing unit 11.

[5-3-2. Scene of Congestion]

Figure 12:
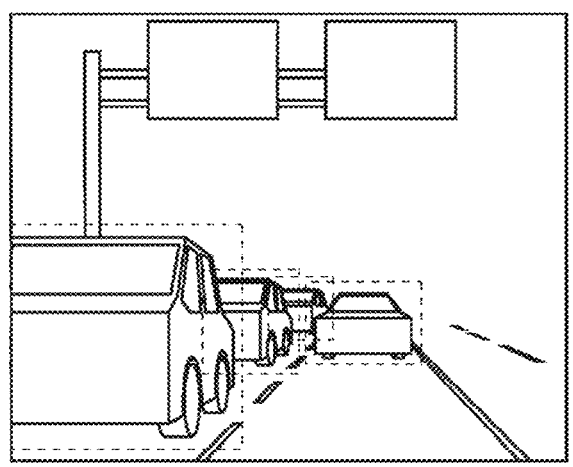
FIG. 12 is a diagram for description of a scene in which the own-vehicle according to the fourth embodiment is caught in a congestion.

FIG. 12 is a diagram for description of a scene in which the own-vehicle is caught in a congestion. As illustrated in FIG. 12, when the own-vehicle is caught in a congestion, a predetermined number or more of other vehicles and the like are included in the view angle of the image capturing unit 11. In such a scene, since it is unlikely that a far object needs to be detected, the scene recognition unit 214 may determine that high-resolution image data is not needed at step S406 in FIG. 10 (NO at step S406).

In addition, since it is desirable to have a detection target range that is wide as possible to detect a suddenly crossing pedestrian or the like in the scene, the scene recognition unit 214 may set the ROI to be the entire view angle of the image capturing unit 11.

Note that since the surrounding situation does not change much in the scene, the scene recognition unit 214 may determine that the frame rate is not set to be high at step S403 in FIG. 10 (NO at step S403). However, the present disclosure is not limited thereto, and the scene recognition unit 214 may determine that the frame rate is set to be high (YES at step S403).

[5-3-3. Scene of Freeway (Straight Road)]

Figure 13:
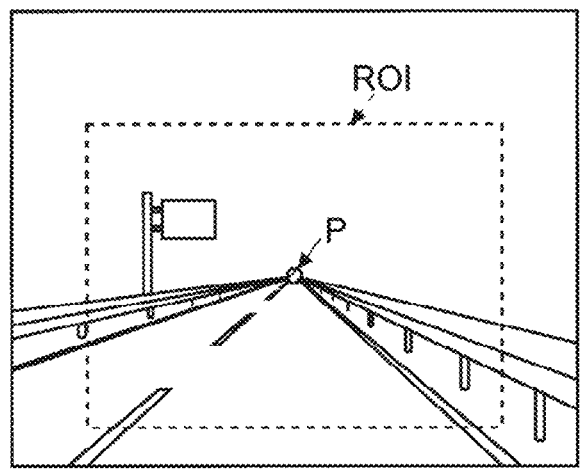

FIG. 13 is a diagram for description of a scene in which the own-vehicle travels on a straight road of a freeway, a tollway, or the like. During traveling on a straight road of a freeway or the like as illustrated in FIG. 13, a far object needs to be detected since the traveling speed of the own-vehicle and the relative speed thereof with respect to other vehicles are fast. Thus, the scene recognition unit 214 may determine that high-resolution image data is needed at step S406 in FIG. 10 (YES at step S406).

In addition, when the traveling speed of the own-vehicle is fast in the scene, it is likely that an image of a peripheral part of the view angle of the image capturing unit 11 is not clearly captured. Thus, the scene recognition unit 214 may set the ROI to be a central part (corresponding to the vehicle front side) in the view angle of the image capturing unit 11. In this case, the scene recognition unit 214 may change the size of the ROI in accordance with the traveling speed of the own-vehicle.

Note that the ROI may be a region centered at an image vanishing point in the view angle. For example, the vanishing point may be calculated by a typical calculation method based on the road shape, a white line on the road, and the like by the scene recognition unit 214. In this case, a learning-completed model may be used.

In addition, in the scene, the scene recognition unit 214 may determine that the frame rate is set to be high at step S403 in FIG. 10 (YES at step S403). However, the present disclosure is not limited thereto, and the scene recognition unit 214 may determine that the frame rate is not set to be high (NO at step S403).

[5-3-4. Scene of Freeway (Curve)]

Figure 14:
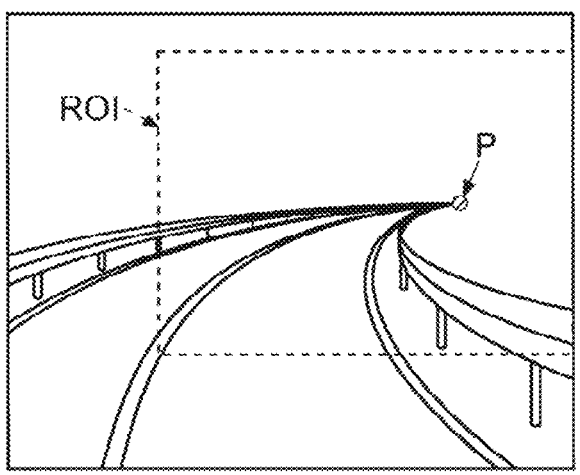

FIG. 14 is a diagram for description of a scene in which the own-vehicle travels on a curve of a freeway, a tollway, or the like. During traveling on a curve of a freeway or the like as illustrated in FIG. 14, similarly to traveling on a straight road of a freeway or the like, the scene recognition unit 214 may determine that high-resolution image data is needed at step S406 in FIG. 10 (YES at step S406) to detect a far object. The scene recognition unit 214 may set the ROI to be a region except for a region, an image of which is not clearly captured.

However, the vanishing point during traveling on a curve is shifted from the center of the view angle to, for example, right or left in accordance with the curvature of the road. Thus, the scene recognition unit 214 may shift the ROI based on the shape of the curve and the like. For example, the ROI may be shifted in accordance with the shift amount of the vanishing point, which can be determined based on the shape of the curve and the like. In this case, the scene recognition unit 214 may determine whether the own-vehicle is traveling on a curve based on input image data and the like. A learning-completed model may be used in this determination.

Note that, in the scene, the scene recognition unit 214 may determine that the frame rate is set to be high at step S403 in FIG. 10 (YES at step S403). However, the present disclosure is not limited thereto, and the scene recognition unit 214 may determine that the frame rate is not set to be high (NO at step S403).

[5-3-5. Scene of Slope]

Figure 15:
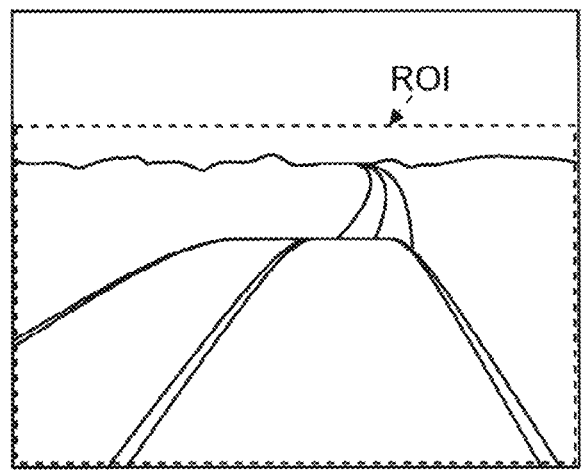
FIG. 15 is a diagram for description of a scene in which the own-vehicle according to the fourth embodiment enters a slope (downslope).

FIG. 15 is a diagram for description of a scene in which the own-vehicle enters a slope (downslope). In a scene in which the own-vehicle enters a slope as illustrated in FIG. 15, the ratio at which a region (region such as sky or sea) not including a detection target such as a road, a road sign, or an oncoming vehicle occupies an image in the view angle is high.

In such a scene in which the ratio of a region including no detection target is high, the scene recognition unit 214 may set the ROI to be a region except for the region including no detection target. In this case, a learning-completed model may be used to specify the region including no detection target.

[5-4. Exemplary Configuration of Switching Between Low-Resolution Readout and High-Resolution Readout]

The following describes, with examples, a configuration for switching between low-resolution readout operation and high-resolution readout operation. Note that the present description is made on an example in which the low-resolution readout operation is achieved by adding the pixel values of adjacent pixels, but the present disclosure is not limited thereto and the low-resolution readout operation may be achieved by skipping (thinning) pixels.

[5-4-1. Exemplary Configuration of Unit Pixel]

Figure 16:
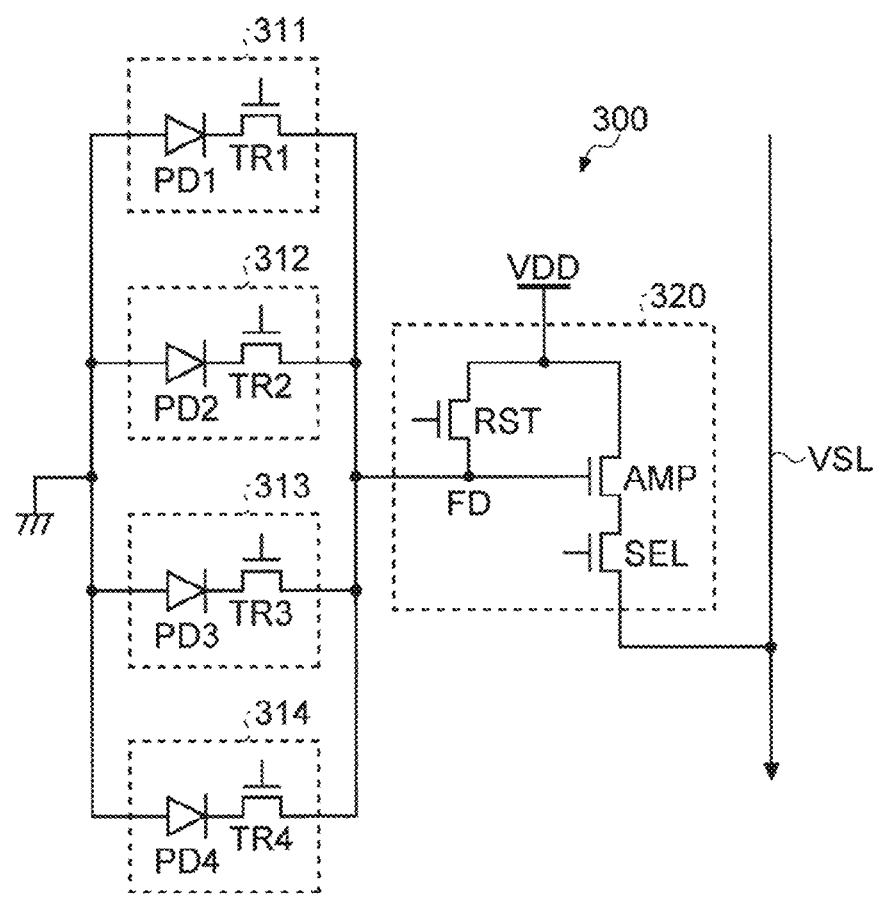
FIG. 16 is a circuit diagram illustrating an exemplary schematic configuration of a unit pixel according to the fourth embodiment.

FIG. 16 is a circuit diagram illustrating an exemplary schematic configuration of a unit pixel according to the present embodiment. As illustrated in FIG. 16, a unit pixel 300 for achieving switching between low-resolution readout and high-resolution readout has, for example, the configuration of a pixel sharing unit including a plurality of pixels (for example, four pixels 311, 312, 313, and 314 in FIG. 16), one-pixel circuit 320 connected with the pixels 311 to 314, and a vertical signal line VSL connected with the pixel circuit 320.

The pixel circuit 320 includes, for example, three transistors, namely, an amplification transistor AMP, a selection transistor SEL, and a reset transistor RST. A node connected with the source of the reset transistor RST and the gate of the amplification transistor AMP functions as a floating diffusion FD configured to accumulate electric charge forwarded from the pixels 311 to 314.

In such a configuration, the unit pixel 300 operates the one-pixel circuit 320 in a time-divided manner to sequentially output pixel signals from the four pixels 311 to 314 to the vertical signal line VSL.

The pixel 311/312/313/314 includes, for example, a photodiode PD1/PD2/PD3/PD4, and a forwarding transistor (also referred to as transfer gate) TR1/TR2/TR3/TR4 connected with the photodiode PD1/PD2/PD3/PD4. In the following description, when not distinguished from one another, the photodiodes PD1 to PD4 are denoted by a reference sign "PD". Similarly, when not distinguished from one another, forwarding transistors TR1 to TR4 are denoted by a reference sign "TR".

The cathode of the photodiode PD, is electrically connected with the source of the forwarding transistor TR, and the anode thereof is electrically connected with a reference potential line (for example, ground). The photodiode PD photoelectrically converts incident light and generates electric charge in accordance with the received-light quantity thereof.

The forwarding transistor TR is, for example, an n-type complementary metal oxide semiconductor (CMOS) transistor. The drain of the forwarding transistor TR is electrically connected with the floating diffusion FD, and the gate thereof is electrically connected with a drive signal line.

The forwarding transistor TR1 forwards the electric charge generated at the photodiode PD to the floating diffusion FD. The floating diffusion FD is an n-type diffusion layer region formed in a p-type semiconductor layer. The floating diffusion FD is an electric charge holding unit configured to temporarily hold the electric charge forwarded from the photodiode PD and is also an electric charge-voltage conversion unit configured to generate voltage in accordance with the amount of the electric charge.

The floating diffusion FD is electrically connected with the gate of the amplification transistor AMP and the source of the reset transistor RST. The gate of the reset transistor RST is connected with a drive signal line. The drain of the reset transistor RST is connected with a power source line VDD.

The gate of the amplification transistor AMP is connected with the floating diffusion FD, the drain of the amplification transistor AMP is connected with the power source line VDD, and the source of the amplification transistor AMP is connected with the drain of the selection transistor SEL. The source of the selection transistor SEL is connected with the vertical signal line VSL, and the gate of the selection transistor SEL is connected with a drive signal line.

When the forwarding transistor TR is turned on, the forwarding transistor TR forwards electric charge at the photodiode PD to the floating diffusion FD. The gate of the forwarding transistor TR includes, for example, what is called a longitudinal electrode and extends from the surface of a semiconductor layer in which the photodiode PD is provided to the depth of the photodiode PD.

The reset transistor RST resets the potential of the floating diffusion FD to be a predetermined potential. When the reset transistor RST is turned on, the potential of the floating diffusion FD is reset to the potential of the power source line VDD.

The selection transistor SEL controls the output timing of a pixel signal from the pixel circuit 320. The amplification transistor AMP generates, as the pixel signal, a signal of voltage in accordance with the level of electric charge held at the floating diffusion FD. The amplification transistor AMP is connected with the vertical signal line VSL through the selection transistor SEL. The amplification transistor AMP forms a source follower together with a load circuit unit connected with the vertical signal line VSL. When the selection transistor SEL is turned on, the amplification transistor AMP generates, on the vertical signal line VSL, a pixel signal of a voltage value in accordance with the voltage of the floating diffusion FD.

The reset transistor RST, the amplification transistor AMP, and the selection transistor SEL may be, for example, N-type CMOS transistors.

The selection transistor SEL may be provided between the power source line VDD and the amplification transistor AMP. In this case, the drain of the reset transistor RST is electrically connected with the power source line VDD and the drain of the selection transistor SEL. The source of the selection transistor SEL is electrically connected with the drain of the amplification transistor AMP.

The source of the amplification transistor AMP (output end of the pixel circuit 320) is electrically connected with the vertical signal line VSL, and the gate of the amplification transistor AMP is electrically connected with the source of the reset transistor RST. Note that although not illustrated, the number of pixels sharing the one-pixel circuit 320 may be other than four. For example, two or eight pixels may share the one-pixel circuit 320.

[5-4-2. Exemplary Pixel Array]

Figure 17:
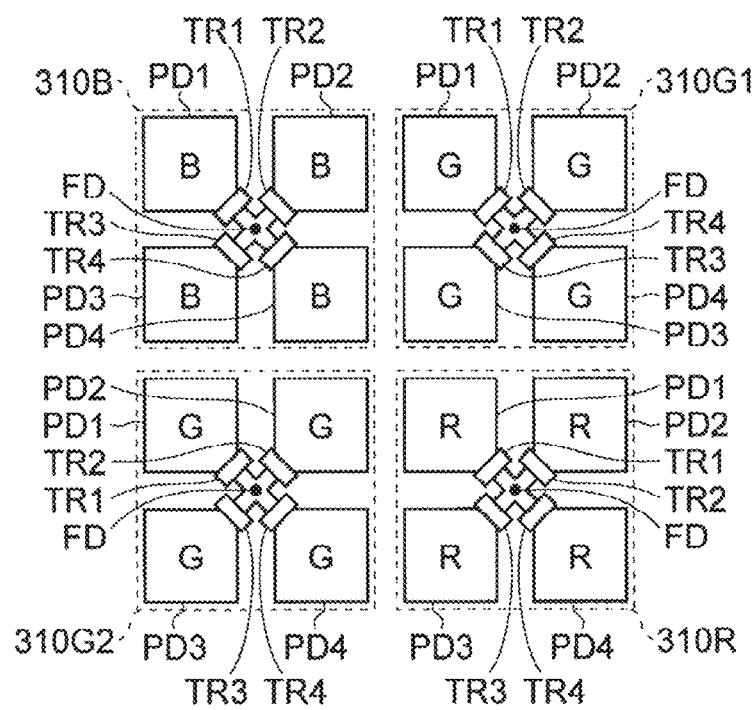
FIG. 17 is a planar layout diagram illustrating an exemplary array of pixels according to the fourth embodiment.

FIG. 17 is a planar layout diagram illustrating an exemplary pixel array according to the present embodiment. Note that although the present description is made on an example in which a unit pixel 310R configured to generate a pixel signal by receiving a red wavelength component, unit pixels 310G1 and 310G2 configured to generate a pixel signal by receiving a green wavelength component, and a unit pixel 310B configured to generate a pixel signal by receiving a blue wavelength component are arrayed in a Bayer array, the wavelength components received by the respective unit pixels and the array thereof are not limited thereto but may be changed in various manners.

As illustrated in FIG. 17, for example, the four pixels 311 to 314 are arrayed in 2×2 pixels in each of the unit pixels 310B, 310G1, 310G2, and 310R. The forwarding transistors TR1 to TR4 of the respective pixels 311 to 314 in each of the unit pixels 310B, 310G1, 310G2, and 310B are disposed at a part across which corners of the photodiodes PD1 to PD4 face each other.

However, the present disclosure is not limited to such a configuration but may be changed in various manners by, for example, interchanging the positions of the pixels 311 to 314 of each of the unit pixels 310B, 310G1, 310G2, and 310R in one unit pattern of the Bayer array.

[5-4-3. Exemplary Timing Chart (High Resolution)]

Figure 18:
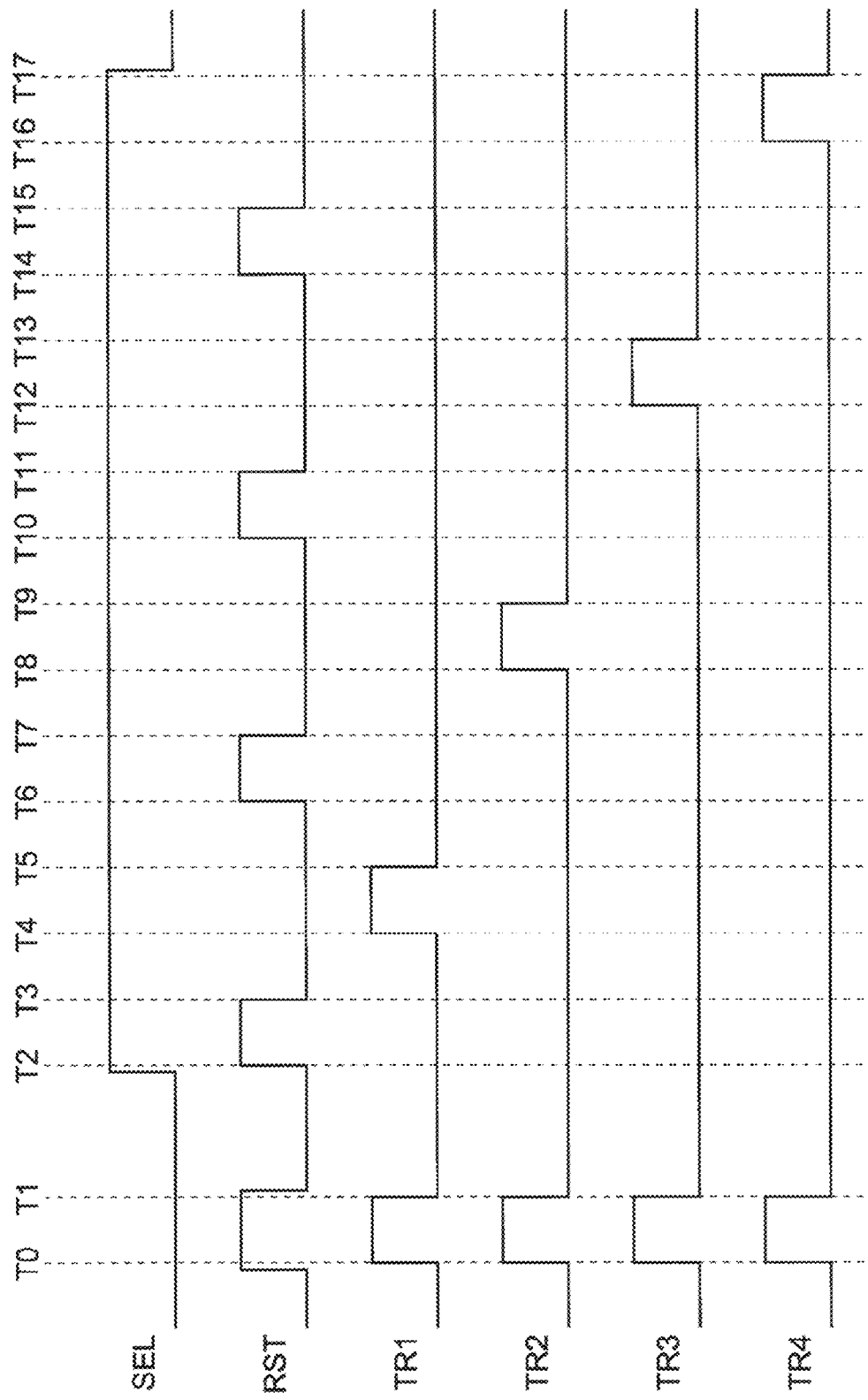
FIG. 18 is a diagram illustrating a timing chart when image data is read at high resolution according to the fourth embodiment.

FIG. 18 is a diagram illustrating a timing chart when image data is read at high resolution. As illustrated in FIG. 18, when image data is read at high resolution, electric charge at the photodiodes PD1 to PD4 is forwarded to the floating diffusion FD in a time-divided manner.

Specifically, when the reset transistor RST and the forwarding transistors TR1 to TR4 are turned on in the duration of timings T0 to T1, electric charge accumulated at the photodiodes PD1 to PD4 and the floating diffusion FD is discharged through the reset transistor RST. Accordingly, electric charge accumulated at the photodiodes PD1 to PD4 so far is discharged, and electric charge obtained through photoelectric conversion of newly incident light is accumulated at the photodiodes PD1 to PD4 in the duration of timings T1 to T4.

Subsequently, the selection transistor SEL is turned on right before timing T2. Accordingly, the unit pixel 300 as a readout target is selected.

Subsequently, the reset transistor RST is turned on in the duration of timings T2 to T3. Accordingly, electric charge accumulated at the floating diffusion FD is discharged, and a voltage level appearing at the vertical signal line VSL is initialized (reset). The voltage level of the vertical signal line VSL in this state is referred to as a reset level. The reset level is subjected to analog-to-digital (AD) conversion and read as a pixel signal of the reset level.

When the reset transistor RST is turned off at timing T5, the floating diffusion FD is electrically disconnected from a power source VDD and becomes floating.

Subsequently, when the forwarding transistor TR1 of the pixel 311 is turned on in the duration of timings T4 to T5, electric charge accumulated at the cathode of the photodiode PD1 is forwarded to the floating diffusion FD through the forwarding transistor TR1. Accordingly, voltage at a voltage value in accordance with the electric charge accumulated at the floating diffusion FD is applied to the gate of the amplification transistor AMP, and as a result, a voltage level in accordance with the electric charge accumulated at the floating diffusion FD appears at the vertical signal line VSL. Hereinafter, the voltage level of the vertical signal line VSL in this state is referred to as a signal level. The signal level is subjected to analog-to-digital (AD) conversion and read as a pixel signal of the signal level.

The difference between the reset level and the signal level read in this manner is calculated to execute correlated double sampling (CDS) processing that removes noise, and accordingly, a pixel signal from which noise is removed is read as a pixel signal of the pixel 311.

Thereafter, in each of the durations of timings T6 to T9, T10 to T13, and T14 to T17, operation same as the operation in the duration of timings T2 to T5 is sequentially executed on the pixels 312 to 314, and accordingly, pixel signals from which noise is removed are read from the pixels 312 to 314.

[5-4-4. Exemplary Timing Chart (Low Resolution)]

Figure 19:
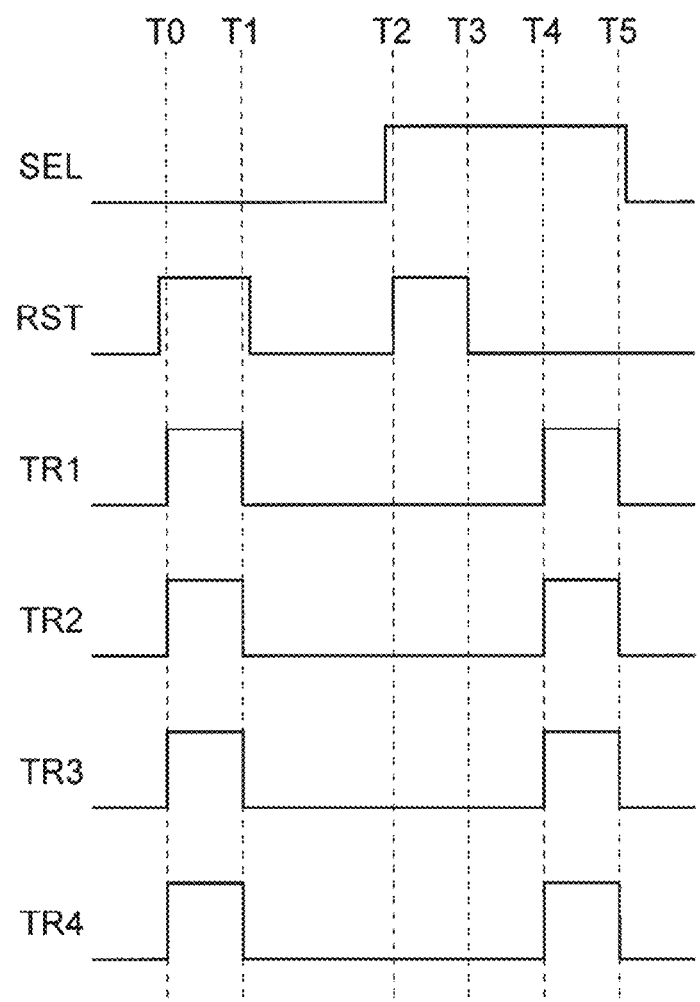
FIG. 19 is a diagram illustrating a timing chart when image data is read at low resolution according to the fourth embodiment.

FIG. 19 is a diagram illustrating a timing chart when image data is read at low resolution. As understood by comparing FIG. 19 with FIG. 18, when image data is read at low resolution, the forwarding transistors TR1 to TR4 of the pixels 311 to 314 are all turned on, for example, in the duration of timings T4 to T5. Accordingly, electric charge accumulated at the cathodes of the respective photodiodes PD1 to PD4 is collectively forwarded to the floating diffusion FD. Specifically, electric charge generated at the photodiodes PD1 to PD4 of the respective pixels 311 to 314 is added at the floating diffusion FD. Accordingly, a pixel signal is read from the pixels 311 to 314 regarded as one pixel in the duration of timings T5 to T6. In this case, the resolution is ¼ times high as in the case of high resolution (refer to FIG. 18).

[5-5. Exemplary Control of Direct Readout of ROI Image from Pixel Array Unit]

The following describes exemplary control when extraction of image data of the ROI is achieved in the image capturing unit 11 in detail with reference to drawings.

Figure 20:
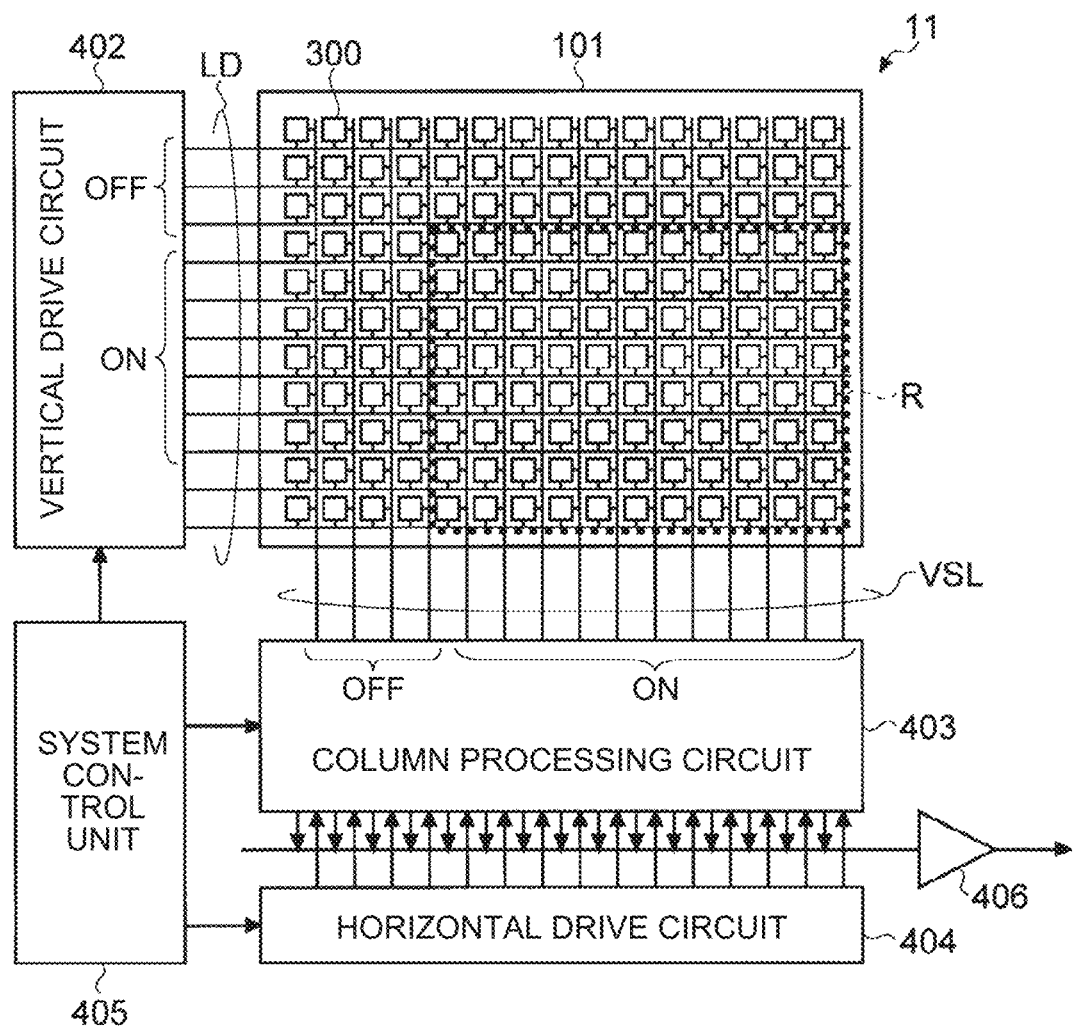
FIG. 20 is a block diagram illustrating an exemplary schematic configuration of an image sensor according to the fourth embodiment.

FIG. 20 is a block diagram illustrating an exemplary schematic configuration of the image sensor according to the present embodiment. As illustrated in FIG. 20, the image sensor 10 includes the pixel array unit 101 and peripheral circuits. The peripheral circuits may include a vertical drive circuit 402, a column processing circuit 403, a horizontal drive circuit 404, a system control unit 405, and an output circuit 406. For example, the vertical drive circuit 402, the horizontal drive circuit 404, and the system control unit 405 may be included in the control unit 12.

The pixel array unit 101 has a configuration in which the unit pixels 300 are disposed in a two-dimensional lattice in row and column directions, in other words, in a matrix of rows and columns. The row direction is a direction (the lateral direction in the drawing) in which pixels are arrayed in a pixel row, and the column direction is a direction (the longitudinal direction in the drawing) in which pixels are arrayed in a pixel column.

In the pixel array in a matrix of rows and columns at the pixel array unit 101, a pixel drive line LD is wired in the row direction for each pixel row, and the vertical signal line VSL is wired in the column direction for each pixel column. The pixel drive line LD transmits a drive signal for performing drive when signals are read from pixels. Although the pixel drive line LD is illustrated as one line in FIG. 20, the present disclosure is not limited to one line. One end of the pixel drive line LD is connected with an output end of the vertical drive circuit 402 corresponding to the row.

The vertical drive circuit 402 is achieved by a shift register, an address decoder, or the like, and drives all pixels of the pixel array unit 101 simultaneously or drives pixels for each row, for example. Thus, the vertical drive circuit 402 functions as a drive unit that controls operation of each pixel of the pixel array unit 101 together with the system control unit 405 that controls the vertical drive circuit 402.

Signals output from respective unit pixels on a pixel row selected and scanned by the vertical drive circuit 402 are input to the column processing circuit 403 through the vertical signal lines VSL of respective pixel columns. The column processing circuit 403 performs, for each pixel column of the pixel array unit 101, predetermined signal processing on a signal output from the corresponding pixel on the selected row through the vertical signal line VSL, and temporarily holds each pixel signal obtained through the signal processing.

Specifically, the column processing circuit 403 performs, as the signal processing, at least noise removal processing such as the CDS processing. For example, the CDS processing removes reset noise and fixed pattern noise unique to a pixel, such as threshold variance of the amplification transistor in the pixel. In addition, the column processing circuit 403 has, for example, an analog-to-digital (AD) conversion function to convert, into a digital signal, an analog pixel signal read and acquired from a photoelectric conversion element and output the digital signal.

The horizontal drive circuit 404 is achieved by a shift register, an address decoder, or the like and sequentially selects the pixel circuits 320 corresponding to each pixel column of the column processing circuit 403. Through this selection scanning by the horizontal drive circuit 404, pixel signals provided with the signal processing for the respective pixel circuits 320 at the column processing circuit 403 are sequentially output.

The system control unit 405 is achieved by, for example, a timing generator configured to generate various timing signals and performs drive control of the vertical drive circuit 402, the column processing circuit 403, the horizontal drive circuit 404, and the like based on the various timings generated at the timing generator. The system control unit 405 may be same as the control unit 12 in FIG. 9.

The output circuit 406 outputs, as image data of one frame, the pixel signals output from the column processing circuit 403.

When extraction of image data of the ROI is achieved in the image capturing unit 11 in the above-described configuration, pixel-signal readout operation is executed only for a region R corresponding to the ROI. Such partial readout operation can be achieved, for example, by activating (turning on) only some pixel drive lines LD corresponding to the ROI in the vertical drive circuit 402 and by operating (turning on) only some ADCs corresponding to the ROI in the column processing circuit 403.

[5-6. Effects]

As described above, in the present embodiment, the image capturing device 1 according to the above-described embodiment is mounted as an on-board camera on a vehicle. Accordingly, necessary image data can be read through optimum readout control in accordance with a scene. As a result, an appropriate vehicle control signal can be generated in accordance with the scene, and thus more appropriate vehicle control can be achieved.

In addition, with the configuration in which image data of a necessary region is output in accordance with a scene, the amount of data to be processed can be reduced, and thus subsequent object detection processing, vehicle control signal generation processing, and the like can be speeded up. Moreover, since the scene recognition unit is disposed in the image sensor 10, control of the image capturing unit can be executed without delay.

Other configurations, operation, and effects may be same as those of the above-described embodiment, and thus detailed description thereof is omitted.

6. Chip Configuration of Image Sensor

The following describes an exemplary chip configuration of the image sensor 10 illustrated in FIG. 1 below in detail with reference to the accompanying drawings.

Figure 21:
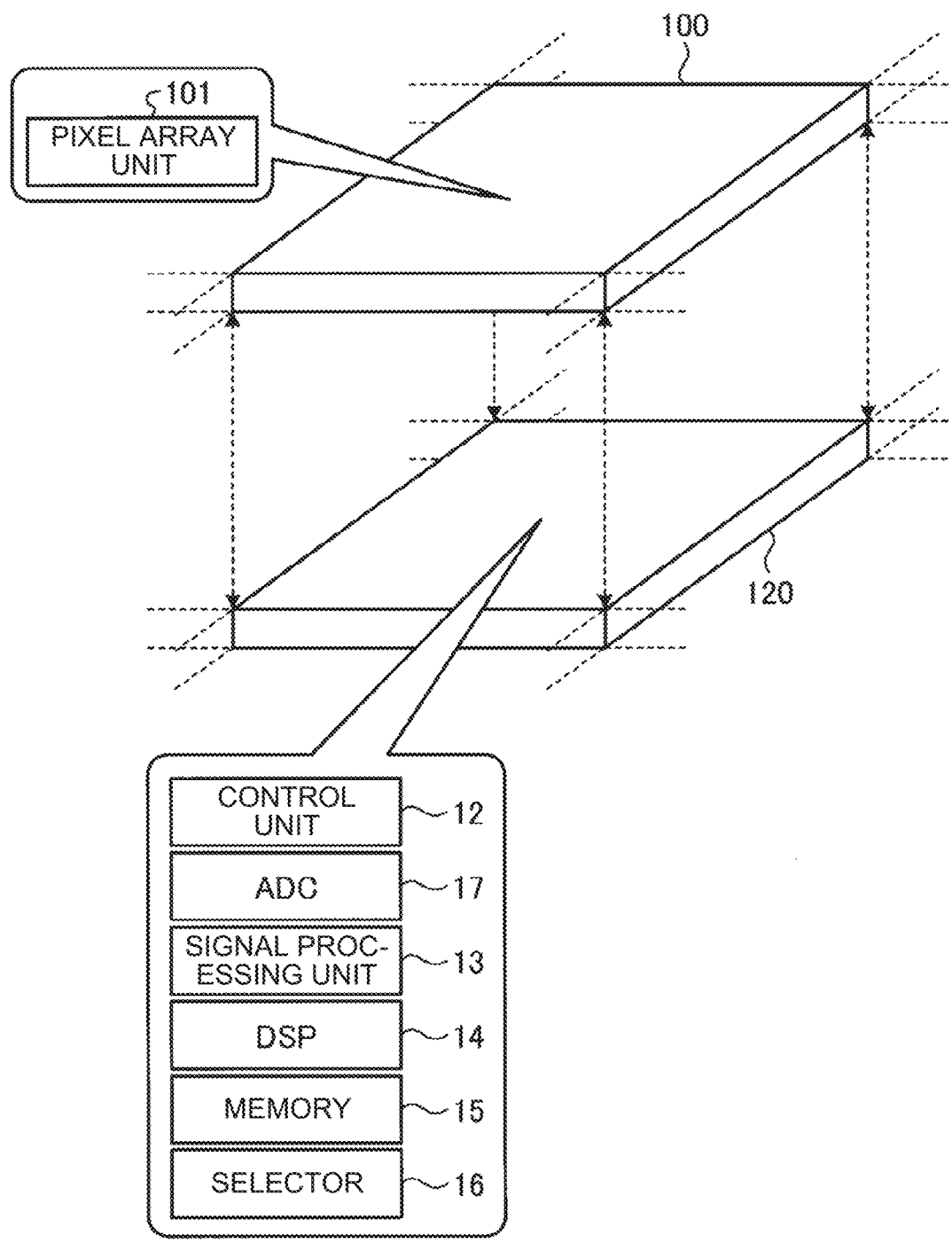
FIG. 21 is a schematic diagram illustrating an exemplary chip configuration of the image sensor according to the present embodiment.

FIG. 21 is a schematic diagram illustrating an exemplary chip configuration of the image sensor according to the present embodiment. As illustrated in FIG. 21, the image sensor 10 has a laminated structure in which a first substrate (die) 100 of a rectangular flat plate shape and a second substrate (die) 120 of a rectangular flat plate shape are bonded to each other.

For example, the first substrate 100 and the second substrate may have the same size. The first substrate 100 and the second substrate 120 may be each a semiconductor substrate such as a silicon substrate.

The pixel array unit 101 of the image capturing unit 11 in the configuration of the image sensor 10 illustrated in FIG. 1 is disposed on the first substrate 100. In addition, part or all of the optical system 104 may be provided on the first substrate 100 in an on-chip manner.

The ADC 17, the control unit 12, the signal processing unit 13, the DSP 14, the memory 15, and the selector 16 in the configuration of the image sensor 10 illustrated in FIG. 1 are disposed on the second substrate 120. Note that an interface circuit and a driver circuit (not illustrated) may be disposed on the second substrate 120.

The bonding of the first substrate 100 and the second substrate 120 may be achieved by what is called a chip-on-chip (CoC) scheme in which the first substrate 100 and the second substrate 120 are each divided into a chip, and then, the divided first substrate 100 and second substrate 120 are bonded to each other, by what is called a chip-on-wafer (CoW) scheme in which one (for example, the first substrate 100) of the first substrate 100 and the second substrate 120 is divided into a chip, and then, the divided first substrate 100 is bonded to the second substrate 120 yet to be divided (in other words, as a wafer), or by what is called a wafer-on-wafer (WoW) scheme in which the first substrate 100 and the second substrate 120 as wafers are bonded to each other.

The first substrate 100 and the second substrate 120 may be joined together by, for example, plasma joining. However, the present disclosure is not limited thereto, but various kinds of joining methods may be used.

7. Exemplary Arrangement

Figure 22:
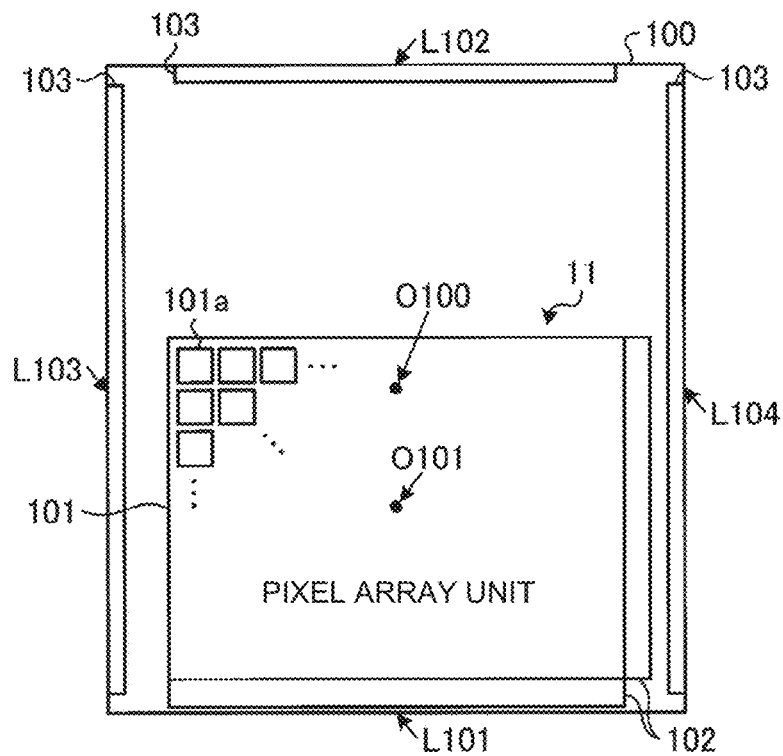
FIG. 22 is a diagram for description of an exemplary arrangement according to the present embodiment.
Figure 23:
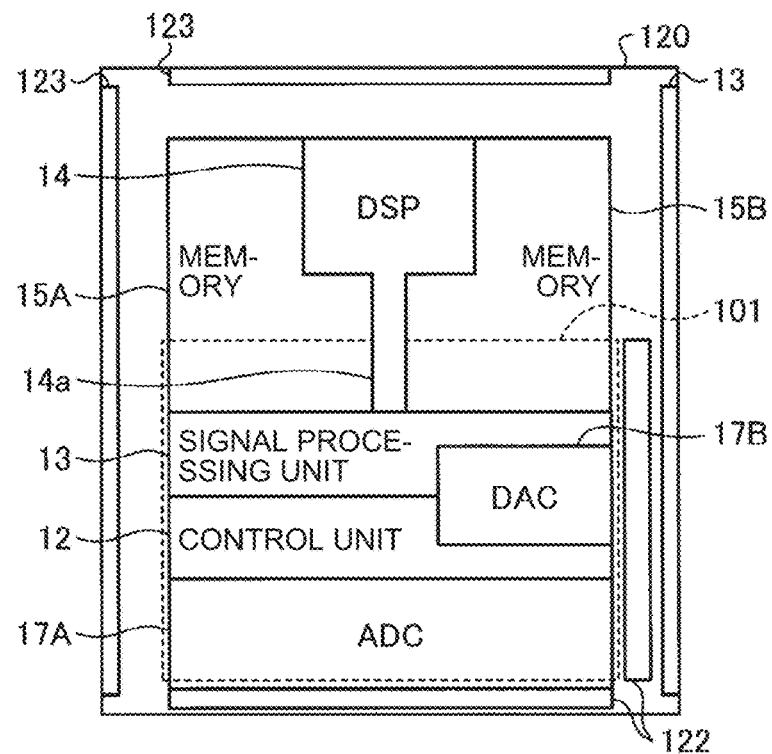
FIG. 23 is a diagram for description of the exemplary arrangement according to the present embodiment.

FIGS. 22 and 23 are each a diagram for description of exemplary arrangement according to the present embodiment. Note that FIG. 22 illustrates exemplary arrangement of the first substrate 100, and FIG. 23 illustrates exemplary arrangement of the second substrate 120.

[7-1. Exemplary Arrangement of First Substrate]

As illustrated in FIG. 22, the pixel array unit 101 of the image capturing unit 11 in the configuration of the image sensor 10 illustrated in FIG. 1 is disposed on the first substrate 100. Note that when part or all of the optical system 104 is mounted on the first substrate 100, the optical system 104 is provided at a position corresponding to the pixel array unit 101.

The pixel array unit 101 is disposed closer to one side L101 among four sides L101 to L104 of the first substrate 100. In other words, the pixel array unit 101 is disposed so that a central part O101 thereof is closer to the side L101 than a central part O100 of the first substrate 100. Note that when a surface of the first substrate 100 on which the pixel array unit 101 is provided is rectangular, the side L101 may be, for example, a shorter side. However, the present disclosure is not limited thereto, and the pixel array unit 101 may be disposed closer to a longer side.

A TSV array 102 in which a plurality of penetration wires (through-silicon via; hereinafter referred to as TSV) penetrating through the first substrate 100 are arrayed as wires for electrically connecting each unit pixel 101a in the pixel array unit 101 with the ADC 17 disposed on the second substrate 120 is provided in a region close to the side L101 among the four sides of the pixel array unit 101, in other words, a region between the side L101 and the pixel array unit 101. In this manner, when the TSV array 102 is provided close to the side L101 to which the pixel array unit 101 is close, it is easy to ensure a disposition space for each component such as the ADC 17 on the second substrate 120.

Note that another TSV array 102 may be provided in a region close to the side L104 (or the side L103) among the two sides L103 and L104 intersecting the side L101, in other words, a region between the side L104 (or the side L103) and the pixel array unit 101.

A pad array 103 in which a plurality of pads are arrayed straight is provided to each of the sides L102 and L103 to which the pixel array unit 101 is not disposed close among the four sides L101 to L104 of the first substrate 100. The pads included in the pad array 103 are, for example, a pad (also referred to as a power source pin) to which power voltage for analog circuits such as the pixel array unit 101 and the ADC 17 is applied, a pad (also referred to as a power source pin) to which power voltage for digital circuits such as the signal processing unit 13, the DSP 14, the memory 15, the selector 16, and the control unit 12 is applied, a pad (also referred to as a signal pin) for interfaces such as a mobile industry processor interface (MIPI) and a serial peripheral interface (SPI), and a pad (also referred to as a signal pin) for clock and data inputting and outputting. Each pad is electrically connected with, for example, an external power circuit or interface circuit through a wire. It is preferable that the pad array 103 and the TSV array 102 are sufficiently separated from each other so that influence of signal reflection from a wire connected with each pad in the pad array 103 is negligible.

[7-2. Exemplary Arrangement of Second Substrate]

As illustrated in FIG. 23, the ADC 17, the control unit 12, the signal processing unit 13, the DSP 14, and the memory 15 in the configuration of the image sensor 10 illustrated in FIG. 1, are disposed on the second substrate 120. Note that in first exemplary arrangement, the memory 15 is divided into two regions of a memory 15A and a memory 15B. Similarly, the ADC 17 is divided into two regions of an ADC 17A and a digital-to-analog converter (DAC) 17B. The DAC 17B is configured to supply reference voltage for AD conversion to the ADC 17A and included as part of the ADC 17 in a broad sense. Although not illustrated in FIG. 22, the selector 16 is disposed on the second substrate 120.

In addition, a wire 122 contacting and electrically connected with each TSV in the TSV array 102 (hereinafter simply referred to as the TSV array 102), which penetrates through the first substrate 100, and a pad array 123, in which a plurality of pads electrically connected with the respective pads in the pad array 103 of the first substrate 100 are arrayed straight, are provided on the second substrate 120.

The TSV array 102 and the wire 122 may be connected with each other by, for example, what is called a twin TSV scheme in which the two TSVs of a TSV provided to the first substrate 100 and a TSV provided from the first substrate 100 to the second substrate 120 are connected on the outer surface of a chip, or what is called a shared TSV scheme in which the connection is achieved through a common TSV provided from the first substrate 100 to the second substrate 120. However, the present disclosure is not limited to these schemes, and may employ various kinds of connection forms such as what is called a Cu—Cu bonding scheme of joining copper (Cu) exposed on a joining surface of the first substrate 100 and copper (Cu) exposed on a joining surface of the second substrate 120.

The form of connection between pads in the pad array 103 of the first substrate 100 and the pad array 123 of the second substrate 120 is, for example, wire bonding. However, the present disclosure is not limited thereto and may employ, for example, a through-hole or castellation connection form.

In the exemplary arrangement of the second substrate 120, for example, when the vicinity of the wire 122 connected with the TSV array 102 is defined to be an upstream side, the ADC 17A, the signal processing unit 13, and the DSP 14 are disposed sequentially from the upstream side along flow of a signal read from the pixel array unit 101. Specifically, the ADC 17A, to which a pixel signal read from the pixel array unit 101 is input first, is disposed close to the wire 122 on the most upstream side, the signal processing unit 13 is subsequently disposed, and the DSP 14 is disposed in a region farthest from the wire 122. With this arrangement in which the ADC 17 to the DSP 14 are disposed along signal flow from the upstream side, wires connecting the components can be shortened. Accordingly, it is possible to achieve signal delay reduction, signal propagation loss reduction, S/N ratio improvement, and electric power consumption reduction.

For example, the control unit 12 is disposed close to the wire 122 on upstream side. In FIG. 22, the control unit 12 is disposed between the ADC 17A and the signal processing unit 13. With such an arrangement, it is possible to reduce signal delay, reduce a signal propagation loss, improve the S/N ratio, and reduce electric power consumption when the control unit 12 controls the pixel array unit 101. In addition, there are an advantage in that signal pins and power source pins for analog circuits can be collectively disposed close to the analog circuits (for example, the lower side in FIG. 22), and signal pins and power source pins for the remaining digital circuits can be collectively disposed close to digital circuits (for example, the upper side in FIG. 22), and an advantage in that power source pins for analog circuits and power source pins for digital circuits can be sufficiently separately disposed.

In the arrangement illustrated in FIG. 22, the DSP 14 is disposed on a side opposite to the ADC 17A on the most downstream side. With such an arrangement, in other words, the DSP 14 can be disposed in a region not overlapping with the pixel array unit 101 in a stacking direction (hereinafter simply referred to as an up-down direction) of the first substrate 100 and the second substrate 120.

With this configuration in which the pixel array unit 101 and the DSP 14 do not overlap with each other in the up-down direction, it is possible to reduce the amount of noise generated when the DSP 14 executes signal processing and entering the pixel array unit 101. As a result, when the DSP 14 is operated as a processing unit configured to execute calculation based on a learning-completed model, it is possible to reduce the amount of noise generated due to signal processing by the DSP 14 and entering the pixel array unit 101, and thus it is possible to acquire an image with reduced quality degradation.

Note that the DSP 14 and the signal processing unit 13 are connected with each other through a connection unit 14a constituted by part of the DSP 14 or a signal line. The selector 16 is disposed, for example, close to the DSP 14. When the connection unit 14a is part of the DSP 14, the DSP 14 partially overlaps with the pixel array unit 101 in the up-down direction, but in such a case as well, it is possible to reduce the amount of noise entering the pixel array unit 101 as compared to a case in which the DSP 14 entirely overlaps with the pixel array unit 101 in the up-down direction.

For example, the memories 15A and 15B are disposed to surround the DSP 14 in three directions. In this manner, when the memories 15A and 15B are disposed to surround the DSP 14, it is possible to average the wiring distance between each memory element on the memory 15 and the DSP 14 and shorten the total distance. Accordingly, it is possible to reduce signal delay, a signal propagation loss, and electric power consumption when the DSP 14 accesses the memory 15.

For example, the pad array 123 is disposed at a position on the second substrate 120, which corresponds to the pad array 103 of the first substrate 100 in the up-down direction. Among the pads included in the pad array 123, pads positioned close to the ADC 17A are used for propagation of power voltage and analog signals for analog circuits (mainly, the ADC 17A). Pads positioned close to the control unit 12, the signal processing unit 13, the DSP 14, and the memories 15A and 15B are used for propagation of power voltage and digital signals for digital circuits (mainly, the control unit 12, the signal processing unit 13, the DSP 14, and the memories 15A and 15B). With such pad arrangement, it is possible to shorten the distance on a wire connecting each pad and each component. Accordingly, it is possible to reduce signal delay, reduce propagation losses of signals and power voltage, improve the S/N ratio, and reduce electric power consumption.

8. Other Embodiments

The above-described processing according to the embodiments may be performed in various kinds of different forms other than the above-described embodiments.

For example, the fabrication processing may execute various kinds of processing in accordance with contents learned by a learning model other than the processing described in the above-described embodiments. For example, it is possible to not only extract the entire face, but also extract the outline of the face, extract only a part such as an eye or nose, extract the owner of the image capturing device 1 or a particular person, or extract a part such as a nameplate or a window from an image of a house. In addition, it is possible to extract an outdoor part photographed in indoor image data, distinguish and extract a human and an animal, or extract a part corresponding to a window from image data. Examples of the fabrication processing include processing of reading only an extracted specific region such as a face, not reading only a specific region, coloring a specific region in black, and reading an image obtained by clipping a specific region. Extraction is not limited to a rectangular region but may be performed on an optional region such as a triangular region. The fabrication processing such as masking processing and mosaic processing is not limited to one piece of processing but may be a combination of a plurality of pieces of processing. Extraction of a face position or the like is not limited to the DSP 14 but may be executed by the signal processing unit 13.

Although the above embodiments describe an example of a learning model learned through a DNN, various neural networks such as a recurrent neural network (RNN) and a convolutional neural network (CNN) may be used other than a DNN. The present disclosure is not limited to a learning model using a DNN or the like, but learning models learned by other various kinds of machine learning of a decision tree, a support vector machine, and the like may be used.

Information including processing procedures, control procedures, specific names, and various kinds of data and parameters described in the above specification and drawings may be optionally changed unless otherwise stated. In addition, specific examples, distribution, numerical values, and the like described in the embodiments are merely exemplary and may be optionally changed.

Components of devices illustrated in the drawings represent conceptual functions and are not necessarily physically configured as illustrated in the drawings. In other words, specific forms of dispersion and integration of the devices are not limited to the illustrated forms, and all or some of the devices may be functionally or physically dispersed and integrated in optional units in accordance with various loads and use situations. For example, the control unit 12 and the signal processing unit 13 illustrated in FIG. 1 may be integrated.

9. Exemplary Application to Moving Object

The technology (present technology) of the present disclosure is applicable to various products. For example, the technology of the present disclosure may be achieved as a device mounted on any kind of a moving object such as an automobile, an electric vehicle, a hybrid electric vehicle, an automatic two-wheel vehicle, a bicycle, a personal mobility, an airplane, a drone, a ship, or a robot.

Figure 24:
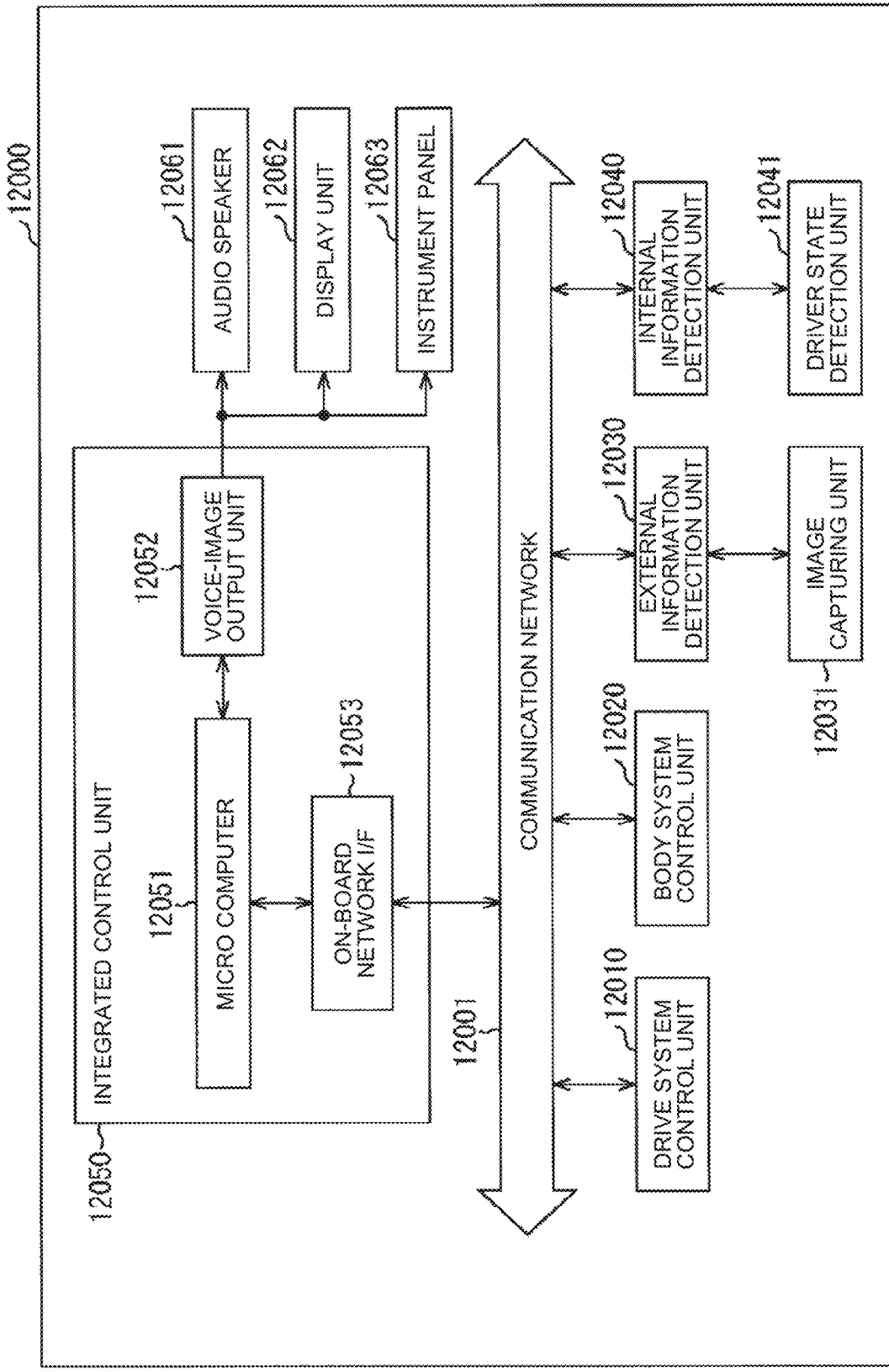
FIG. 24 is a block diagram illustrating an exemplary schematic configuration of a vehicle control system.

FIG. 24 is a block diagram illustrating an exemplary schematic configuration of a vehicle control system as an exemplary moving object control system to which the technology of the present disclosure is applicable.

This vehicle control system 12000 includes a plurality of electronic control units connected with each other through a communication network 12001. In the example illustrated in FIG. 24, the vehicle control system 12000 includes a drive system control unit 12010, a body system control unit 12020, an external information detection unit 12030, an internal information detection unit 12040, and an integrated control unit 12050. In addition, a microcomputer 12051, a voice-image output unit 12052, and an on-board network I/F (interface) 12053 are illustrated as a functional configuration of the integrated control unit 12050.

The drive system control unit 12010 controls operation of devices related to a drive system of a vehicle in accordance with various computer programs. For example, the drive system control unit 12010 functions as a control device for a drive power generation device, such as an internal combustion engine or a drive motor, for generating drive power of the vehicle, a drive power transmission mechanism for transferring the drive power to wheels, a steering mechanism configured to adjust the rudder angle of the vehicle, a braking device configured to generate braking force of the vehicle, and the like.

The body system control unit 12020 controls operation of various devices installed on a vehicle body in accordance with various computer programs. For example, the body system control unit 12020 functions as a control device for a keyless entry system, a smart key system, a power window device, and various lamps such as a head lamp, a rear lamp, a brake lamp, an indicator, and a fog lamp. In this case, the body system control unit 12020 can receive radio wave transmitted from a portable device serving as a key, or various switch signals. The body system control unit 12020 receives input of the radio wave or signals and controls a door lock device, a power window device, a lamp, and the like of the vehicle.

The external information detection unit 12030 detects information on the outside of the vehicle on which the vehicle control system 12000 is mounted. For example, the external information detection unit 12030 is connected with an image capturing unit 12031. The external information detection unit 12030 causes the image capturing unit 12031 to capture an external image and receives the captured image. The external information detection unit 12030 may perform, based on the received image, object detection processing or distance detection processing for a person, a car, an obstacle, a sign, a character on a road surface, and the like.

The image capturing unit 12031 is a light sensor configured to receive light and output an electric signal in accordance with the received-light quantity of the light. The image capturing unit 12031 may output the electric signal as an image or may output the electric signal as distance measurement information. Light received by the image capturing unit 12031 may be visible light or invisible light such as infrared.

The internal information detection unit 12040 detects internal information. The internal information detection unit 12040 is connected with, for example, a driver state detection unit 12041 configured to detect the state of a driver. The driver state detection unit 12041 includes a camera configured to capture an image of the driver, for example, and the internal information detection unit 12040 may calculate the degree of fatigue or concentration of the driver or determine whether the driver is dozing based on detection information input from the driver state detection unit 12041.

The microcomputer 12051 can calculate a control target value of the drive power generation device, the steering mechanism, or the braking device based on the internal and external information acquired by the external information detection unit 12030 and the internal information detection unit 12040, and can output a control command to the drive system control unit 12010. For example, the microcomputer 12051 can perform cooperative control to achieve functions of an advanced driver assistance system (ADAS) including collision avoidance or impact reduction of the vehicle, follow travel based on inter-vehicular distance, vehicle speed maintaining travel, warning for collision of the vehicle, warning for lane deviation of the vehicle, or the like.

The microcomputer 12051 can perform cooperative control for, for example, automated driving in which the vehicle travels autonomously independent from operation by the driver by controlling the drive power generation device, the steering mechanism, the braking device, and the like based on information on surroundings of the vehicle, which is acquired by the external information detection unit 12030 and the internal information detection unit 12040.

The microcomputer 12051 can output a control command to the body system control unit 12020 based on the external information acquired by the external information detection unit 12030. For example, the microcomputer 12051 can control the head lamp in accordance with the position of a preceding vehicle or oncoming vehicle sensed by the external information detection unit 12030, and can perform cooperative control to achieve dimming such as switching from high beam to low beam.

The voice-image output unit 12052 transmits an output signal of at least one of voice and image to an output device capable of visually or audibly giving notification of information to a person on board the vehicle or the outside. In the example of FIG. 24, an audio speaker 12061, a display unit 12062, and an instrument panel 12063 are exemplarily illustrated as the output device. The display unit 12062 may include, for example, at least one of an on-board display and a head-up display.

Figure 25:
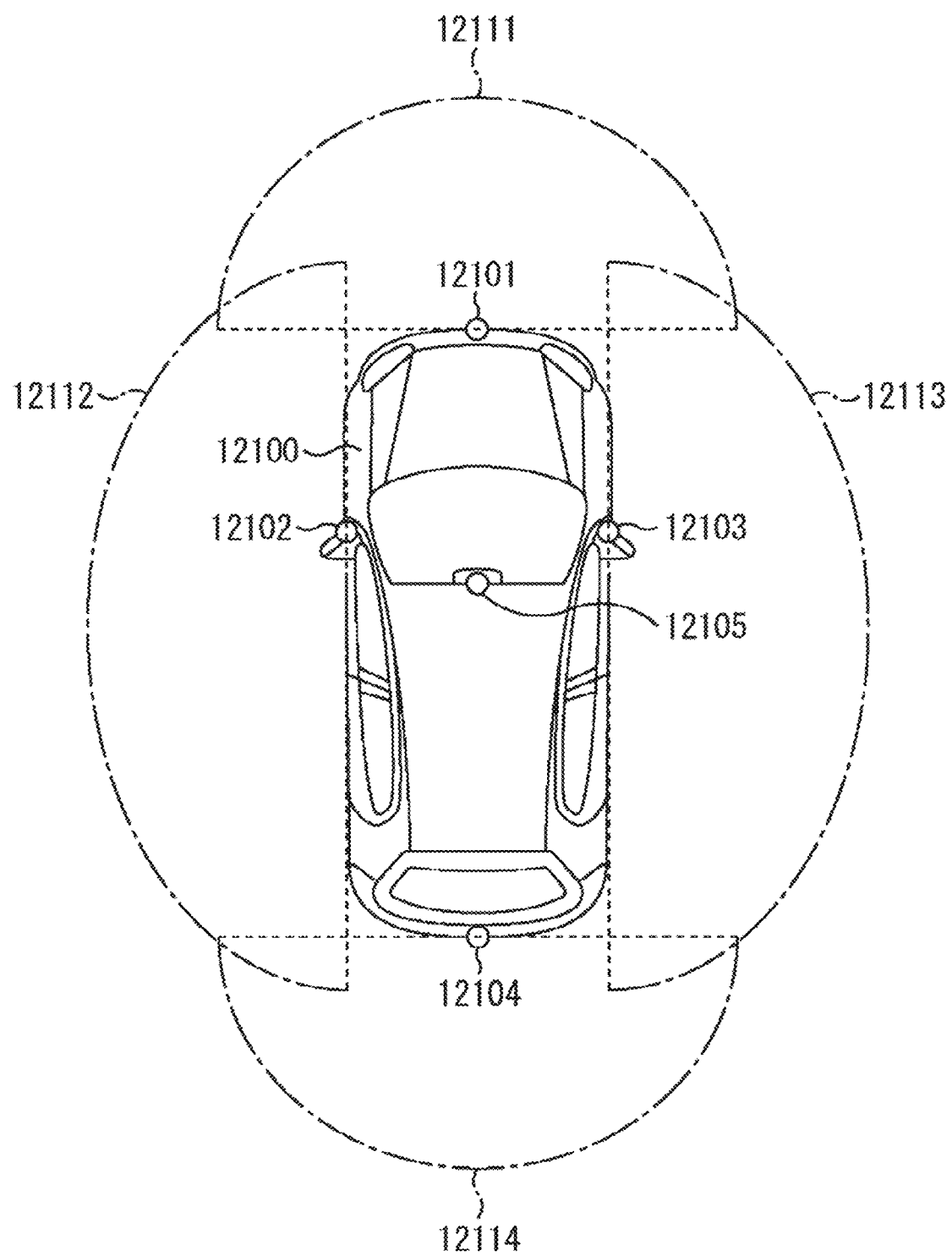
FIG. 25 is an explanatory diagram illustrating exemplary installation positions of an external information detection unit and an image capturing unit.

FIG. 25 is a diagram illustrating an exemplary installation position of the image capturing unit 12031.

In FIG. 25, image capturing units 12101, 12102, 12103, 12104, and 12105 are provided as the image capturing unit 12031.

The image capturing units 12101, 12102, 12103, 12104, and 12105 are provided at positions, for example, the front nose, the side mirrors, the rear bumper, and the rear door of a vehicle 12100, an upper part of the front glass in the vehicle, and the like. The image capturing unit 12101 provided at the front nose and the image capturing unit 12105 provided at the upper part of the front glass in the vehicle mainly acquire images of the front side of the vehicle 12100. The image capturing units 12102 and 12103 provided at the side mirrors mainly acquire images of the sides of the vehicle 12100. The image capturing unit 12104 provided at the rear bumper or the rear door mainly acquires an image of the back side of the vehicle 12100. The image capturing unit 12105 provided inside at an upper part of the front glass is mainly used to detect a preceding vehicle, a pedestrian, an obstacle, a traffic light, a traffic sign, a lane, or the like.

Note that FIG. 25 illustrates exemplary image capturing ranges of the image capturing units 12101 to 12104. An image capturing range 12111 indicates the image capturing range of the image capturing unit 12101 provided at the front nose, image capturing ranges 12112 and 12113 indicate the image capturing ranges of the image capturing units 12102 and 12103 provided at the respective side mirrors, and an image capturing range 12114 indicates the image capturing range of the image capturing unit 12104 provided at the rear bumper or the rear door. For example, image data captured by the image capturing units 12101 to 12104 can be placed together to obtain a panoramic image when the vehicle 12100 is viewed from above.

At least one of the image capturing units 12101 to 12104 may have a function of acquiring distance information. For example, at least one of the image capturing units 12101 to 12104 may be a stereo camera made of a plurality of image sensors or may be an image sensor including pixels for phase difference detection.

For example, the microcomputer 12051 calculates the distance to each stereoscopic object in the image capturing ranges 12111 to 12114 and temporal change (speed relative to the vehicle 12100) of the distance based on distance information obtained from the image capturing units 12101 to 12104, thereby extracting, as a preceding vehicle, in particular, a stereoscopic object that is nearest on the traveling path of the vehicle 12100 and traveling at a predetermined speed (for example, equal to or higher than 0 km/h) in a direction substantially same as that of the vehicle 12100. In addition, the microcomputer 12051 sets an inter-vehicular distance to be ensured to a preceding vehicle in advance, thereby performing automatic brake control (including follow stop control), automatic acceleration control (including follow start control), and the like. In this manner, it is possible to perform cooperative control for, for example, automated driving in which the vehicle travels autonomously independent from operation by the driver.

For example, the microcomputer 12051 can classify, based on distance information obtained from the image capturing units 12101 to 12104, stereoscopic object data related to a stereoscopic object into a two-wheel vehicle, a standard-size vehicle, a large-size vehicle, a pedestrian, a utility pole, and other stereoscopic objects, extract the stereoscopic object data, and use the stereoscopic object data for obstacle automatic avoidance. For example, the microcomputer 12051 identifies an obstacle in surroundings of the vehicle 12100 as an obstacle that is visually recognizable by the driver of the vehicle 12100 or an obstacle difficult to be visually recognized. Then, the microcomputer 12051 determines a collision risk indicating a danger degree of collision with each obstacle, and in a situation in which the collision risk is equal to or larger than a set value and collision is likely to happen, the microcomputer 12051 can perform operation support for collision avoidance by outputting an alert to the driver through the audio speaker 12061 and the display unit 12062 or performing forced deceleration and avoidance steering through the drive system control unit 12010.

At least one of the image capturing units 12101 to 12104 may be an infrared camera configured to detect infrared. For example, the microcomputer 12051 can recognize a pedestrian by determining whether the pedestrian exists in images captured by the image capturing units 12101 to 12104. This pedestrian recognition is performed through, for example, a procedure of extracting feature points in images captured by the image capturing units 12101 to 12104 as infrared cameras, and a procedure of determining whether an object is a pedestrian by performing pattern matching processing on a series of feature points indicating the outline of the object. When the microcomputer 12051 determines that a pedestrian exists in the images captured by the image capturing units 12101 to 12104 and recognizes the pedestrian, the voice-image output unit 12052 controls the display unit 12062 to display the recognized pedestrian in superimposition with a rectangular outline line for enhancement. The voice-image output unit 12052 may control the display unit 12062 to display an icon or the like illustrating the pedestrian at a desired position.

The above description is made on an example of the vehicle control system to which the technology of the present disclosure is applicable. The technology of the present disclosure is applicable to the image capturing unit 12031 and the like among the above-described components. When the technology of the present disclosure is applied to the image capturing unit 12031 and the like, it is possible to achieve size reduction of the image capturing unit 12031 and the like, which facilitates interior and exterior designing of the vehicle 12100. In addition, when the technology of the present disclosure is applied to the image capturing unit 12031 and the like, it is possible to acquire a clear image with reduced noise and thus provide a more easily viewable captured image to the driver. Accordingly, fatigue of the driver can be reduced.

10. Exemplary Application to Endoscope Operation System

The technology (present technology) of the present disclosure is applicable to various products. For example, the technology of the present disclosure may be applied to an endoscope operation system.

Figure 26:
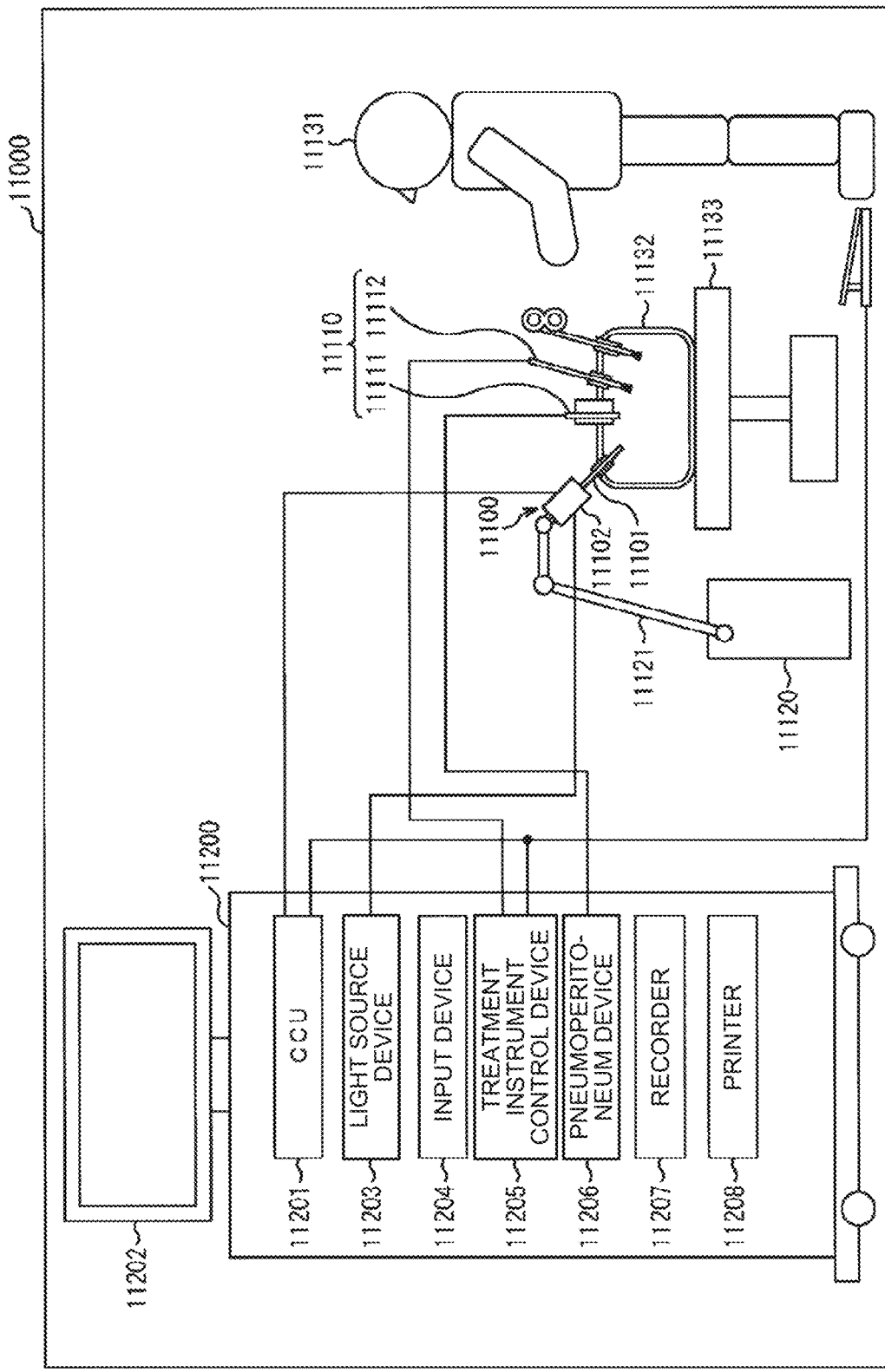
FIG. 26 is a diagram illustrating an exemplary schematic configuration of an endoscope operation system.

FIG. 26 is a diagram illustrating an exemplary schematic configuration of an endoscope operation system to which the technology (present technology) of the present disclosure is applicable.

FIG. 26 illustrates a situation in which an operator (doctor) 11131 performs a medical operation on a patient 11132 on a patient bed 11133 by using this endoscope operation system 11000. As illustrated in FIG. 26, the endoscope operation system 11000 includes an endoscope 11100, other operation instruments 11110 such as a pneumoperitoneum tube 11111 and an energy treatment instrument 11112, a support arm device 11120 supporting the endoscope 11100, and a cart 11200 on which various devices for an endoscopic medical operation are mounted.

The endoscope 11100 includes a lens barrel 11101, a region of which extending from the leading end by a predetermined length is inserted into the body cavity of the patient 11132, and a camera head 11102 connected with the base end of the lens barrel 11101. In the illustrated example, the endoscope 11100 is configured as what is called a rigid scope including the lens barrel 11101 that is rigid, but the endoscope 11100 may be configured as what is called a flexible scope including a flexible lens barrel.

An opening to which an objective lens is fitted is provided at the leading end of the lens barrel 11101. A light source device 11203 is connected with the endoscope 11100, and light generated by the light source device 11203 is guided to the leading end of the lens barrel 11101 by a light guide extending inside the lens barrel 11101 and is emitted toward an observation target in the body cavity of the patient 11132 through the objective lens. Note that the endoscope 11100 may be a direct-view scope, an oblique-view scope, or a side-view scope.

An optical system and an image capturing element are provided inside the camera head 11102, and reflected light (observation light) from the observation target is condensed onto the image capturing element through the optical system. The observation light is photoelectrically converted by the image capturing element, and an electric signal corresponding to the observation light, in other words, an image signal corresponding to an observation image is generated. The image signal is transmitted to a camera control unit (CCU) 11201 as RAW data.

The CCU 11201 includes a central processing unit (CPU) and a graphics processing unit (GPU), and collectively controls operation of the endoscope 11100 and a display device 11202. In addition, the CCU 11201 receives the image signal from the camera head 11102 and provides the image signal with various image processing, such as image development processing (demosaic processing), for displaying an image based on the image signal.

The display device 11202 displays, under control of the CCU 11201, an image based on the image signal provided with the image processing by the CCU 11201.

The light source device 11203 includes a light source such as a light emitting diode (LED) and supplies, to the endoscope 11100, irradiation light for image capturing of an operation site or the like.

An input device 11204 is an input interface for the endoscope operation system 11000. A user can input various kinds of information and instructions to the endoscope operation system 11000 through the input device 11204. For example, the user inputs an instruction to change image capturing conditions (such as irradiation light kind, magnification, and focal length) of the endoscope 11100.

A treatment instrument control device 11205 controls drive of the energy treatment instrument 11112 for tissue cauterization, incision, blood vessel sealing, or the like. A pneumoperitoneum device 11206 feeds gas into the body cavity through the pneumoperitoneum tube 11111 so that the body cavity of the patient 11132 is inflated to obtain a visual field of the endoscope 11100 and a work space for an operator. A recorder 11207 is a device capable of recording various kinds of information related to the medical operation. A printer 11208 is a device capable of printing various kinds of information related to the medical operation in various formats of text, image, graph, and the like.

Note that the light source device 11203 that supplies irradiation light for image capturing of an operation site to the endoscope 11100 may be achieved by a white light source configured as, for example, an LED, a laser beam source, or a combination thereof. When the white light source is configured as a combination of RGB laser beam sources, the output intensity and output timing of each color (wavelength) can be highly accurately controlled, and thus the white balance of a captured image can be adjusted at the light source device 11203. In addition, in this case, an image corresponding to each of RGB can be captured in a time divisional manner by irradiating an observation target with laser beams from the respective RGB laser beam sources in a time divisional manner and controlling drive of the image capturing elements of the camera head 11102 in synchronization with the timings of irradiation. With this method, a color image can be obtained without providing color filters to the image capturing elements.

In addition, drive of the light source device 11203 may be controlled so that the intensity of output light is changed in every predetermined time. Drive of the image capturing elements of the camera head 11102 is controlled in synchronization with the timing of the light intensity change to acquire images in a time divisional manner. The images can be synthesized to generate a high dynamic range image without what are called underexposure and overexposure.

The light source device 11203 may be capable of supplying light in a predetermined wavelength band for special light observation. In the special light observation, for example, what is called narrow band light observation (narrow band imaging) is performed in which an image of a predetermined tissue such as a blood vessel on the surface layer of mucous membrane is captured at high contrast through irradiation with light in a band narrower than the band of irradiation light (in other words, white light) in normal observation by using the wavelength dependency of light absorption in a body tissue. Alternatively, in the special light observation, fluorescence observation may be performed in which an image is obtained by using fluorescence generated through irradiation with excitation light. In the fluorescence observation, for example, a body tissue is irradiated with excitation light to observe fluorescence from the body tissue (self-fluorescence observation), or a reagent such as indocyanine green (ICG) is locally injected into a body tissue and the body tissue is irradiated with excitation light corresponding to the fluorescence wavelength of the reagent to obtain a fluorescence image. The light source device 11203 may be capable of supplying the narrow band light and/or excitation light corresponding to such special light observation.

Figure 27:
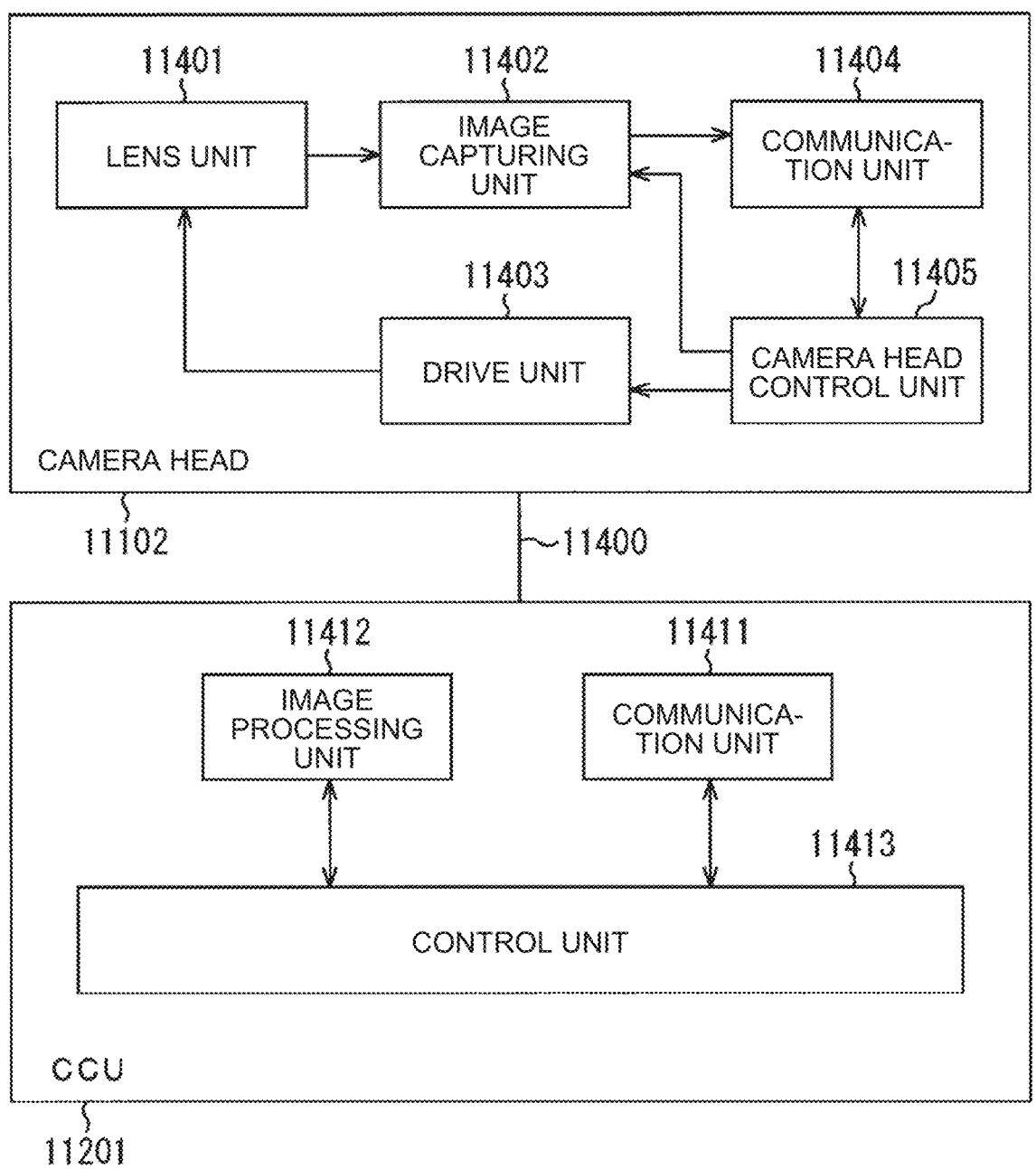
FIG. 27 is a block diagram illustrating an exemplary functional configuration of a camera head and a CCU.

FIG. 27 is a block diagram illustrating exemplary functional configurations of the camera head 11102 and the CCU 11201 illustrated in FIG. 26.

The camera head 11102 includes a lens unit 11401, an image capturing unit 11402, a drive unit 11403, a communication unit 11404, and a camera head control unit 11405. The CCU 11201 includes a communication unit 11411, an image processing unit 11412, and a control unit 11413. The camera head 11102 and the CCU 11201 are connected with each other through a transmission cable 11400 to perform communication therebetween.

The lens unit 11401 is an optical system provided at a connection part with the lens barrel 11101. The observation light acquired from the leading end of the lens barrel 11101 is guided to the camera head 11102 and incident on the lens unit 11401. The lens unit 11401 is formed by combining a plurality of lenses including a zoom lens and a focus lens.

The image capturing unit 11402 may include one image capturing element (what is called a single-plate configuration) or a plurality of image capturing elements (what is called a multiple-plate configuration). When the image capturing unit 11402 has the multiple-plate configuration, for example, image signals corresponding to RGB may be generated by the respective image capturing elements and synthesized to obtain a color image. Alternatively, the image capturing unit 11402 may include a pair of image capturing elements for acquiring right-eye and left-eye image signals, respectively, for three-dimensional (3D) display. When 3D display is performed, the operator 11131 can more accurately understand the depth of a living body tissue at an operation site. Note that when the image capturing unit 11402 has the multiple-plate configuration, a plurality of lens units 11401 are provided for the respective image capturing elements.

The image capturing unit 11402 does not necessarily need to be provided to the camera head 11102. For example, the image capturing unit 11402 may be provided right after the objective lens inside the lens barrel 11101.

The drive unit 11403 is achieved by an actuator and moves each of the zoom and focus lenses of the lens unit 11401 along the optical axis by a predetermined distance under control of the camera head control unit 11405. Accordingly, the magnification and focal point of an image captured by the image capturing unit 11402 can be adjusted as appropriate.

The communication unit 11404 is achieved by a communication device for communicating various kinds of information with the CCU 11201. The communication unit 11404 transmits an image signal acquired from the image capturing unit 11402 to the CCU 11201 through the transmission cable 11400 as RAW data.

The communication unit 11404 receives a control signal for controlling drive of the camera head 11102 from the CCU 11201, and supplies the control signal to the camera head control unit 11405. The control signal includes information related to image capturing conditions, such as information on specification of the frame rate of a captured image, information on specification of an exposure value at image capturing, and/or information on specification of the magnification and focal point of the captured image.

Note that the above-described image capturing conditions such as the frame rate, the exposure value, the magnification, and the focal point may be specified by the user as appropriate or may be automatically set by the control unit 11413 of the CCU 11201 based on the acquired image signal. In the latter case, the endoscope 11100 has what are called an auto exposure (AE) function, an auto focus (AF) function, and an auto white balance (AWB) function.

The camera head control unit 11405 controls drive of the camera head 11102 based on the control signal received from the CCU 11201 through the communication unit 11404.

The communication unit 11411 is achieved by a communication device for communicating various kinds of information with the camera head 11102. The communication unit 11411 receives an image signal transmitted from the camera head 11102 through the transmission cable 11400.

The communication unit 11411 transmits a control signal for controlling drive of the camera head 11102 to the camera head 11102. The image signal and the control signal may be transmitted by electrical communication, optical communication, and the like.

The image processing unit 11412 performs various kinds of image processing on an image signal as RAW data transmitted from the camera head 11102.

The control unit 11413 performs various kinds of control related to image capturing of an operation site or the like by the endoscope 11100 and display of a captured image obtained through image capturing of an operation site or the like. For example, the control unit 11413 generates a control signal for controlling drive of the camera head 11102.

In addition, the control unit 11413 causes the display device 11202 to display a captured image of an operation site or the like based on the image signal on which the image processing is performed by the image processing unit 11412. In this case, the control unit 11413 may recognize various objects in the captured image by using various image recognition technologies. For example, the control unit 11413 detects the edge shape, color, and the like of each object included in the captured image to recognize for example, an operation instrument such as forceps, a particular living body site, bleeding, and mist when the energy treatment instrument 11112 is used. When causing the display device 11202 to display the captured image, the control unit 11413 uses a result of the recognition to display various kinds of operation support information on the image of the operation site in a superimposing manner. When the operation support information is displayed in a superimposing manner and presented to the operator 11131, a load on the operator 11131 can be reduced, and the operator 11131 can reliably perform a medical operation.

The transmission cable 11400 connecting the camera head 11102 and the CCU 11201 is an electric signal cable compatible with electric signal communication, an optical fiber compatible with optical communication, or a composite cable thereof.

In the illustrated example, communication is performed in a wired manner by using the transmission cable 11400, but communication between the camera head 11102 and the CCU 11201 may be performed in a wireless manner.

The above description is made on an exemplary endoscope operation system to which the technology of the present disclosure is applicable. The technology of the present disclosure is applicable to, for example, the image capturing unit 11402 of the camera head 11102 among the above-described components. When the technology of the present disclosure is applied to the camera head 11102, it is possible to achieve size reduction of the camera head 11102 and the like and thus obtain the endoscope operation system 11000 of a compact size. In addition, when the technology of the present disclosure is applied to the camera head 11102 and the like, it is possible to acquire a clear image with reduced noise, and thus provide a more easily viewable captured image to the operator. Accordingly, fatigue of the operator can be reduced.

Note that the above description is made on an example of an endoscope operation system, but the technology of the present disclosure may be applied to, for example, a microscope operation system.

11. Exemplary Application to Whole Slide Imaging (WSI) System

The technology of the present disclosure is applicable to various products. For example, the technology of the present disclosure may be applied to a pathological diagnosis system with which a doctor or the like diagnoses a lesion by observing cells and tissues collected from a patient, and a support system for the diagnosis (hereinafter referred to as a diagnosis support system). The diagnosis support system may be a whole slide imaging (WSI) system that diagnoses a lesion based on an image acquired by using a digital pathology technology or supports the diagnosis.

Figure 28:
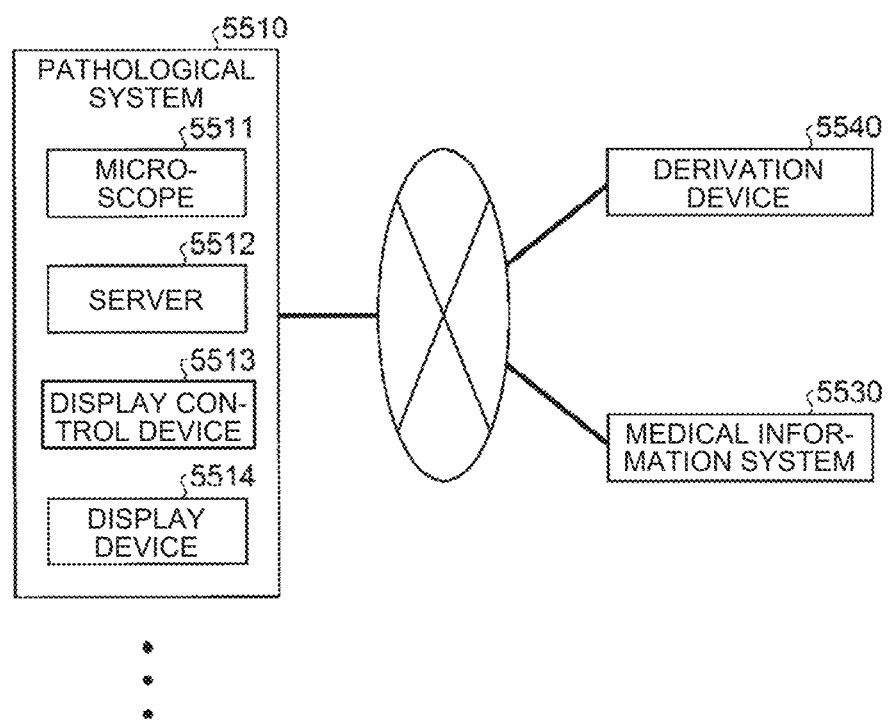
FIG. 28 is a block diagram illustrating an exemplary schematic configuration of a diagnosis support system.

FIG. 28 is a diagram illustrating an exemplary schematic configuration of a diagnosis support system 5500 to which the technology of the present disclosure is applied. As illustrated in FIG. 28, the diagnosis support system 5500 includes one or more pathological systems 5510. The diagnosis support system 5500 may also include a medical information system 5530 and a derivation device 5540.

The one or more pathological systems 5510 are each a system mainly used by a pathologist and installed in, for example, a laboratory or a hospital. The pathological systems 5510 may be installed in hospitals different from each other and each connected with the medical information system 5530 and the derivation device 5540 through various kinds of networks such as a wide area network (WAN) (including the Internet), a local area network (LAN), a public network, and a mobile communication network.

Each pathological system 5510 includes a microscope 5511, a server 5512, a display control device 5513, and a display device 5514.

The microscope 5511 has the function of an optical microscope, performs image capturing of an observation object set in a glass slide, and acquires a pathological image as a digital image. The observation object is, for example, a tissue or a cell collected from a patient or may be a piece of an organ, saliva, or blood.

The server 5512 stores and records the pathological image acquired by the microscope 5511 in a storage unit (not illustrated). When having received a browsing request from the display control device 5513, the server 5512 searches the storage unit (not illustrated) for a pathological image and transfers the searched pathological image to the display control device 5513.

The display control device 5513 transfers a request to browse a pathological image, which is received by a user, to the server 5512. Then, the display control device 5513 displays the pathological image received from the server 5512 on the display device 5514 using a liquid crystal display, an electro-luminescence (EL) display, or a cathode ray tube (CRT) display. Note that the display device 5514 may be compatible with 4K and 8K, and the number of display devices is not limited to one but may be two or more.

When the observation object is a solid matter such as a piece of an organ, the observation object may be, for example, a dyed slice. The slice may be produced by, for example, slicing a block piece cut out from a sample such as an organ. At the slicing, the block piece may be fixed by, for example, paraffin.

The dyeing of the slice may be achieved by various kinds of dyeing, for example, general dyeing to visualize the form of a tissue, such as hematoxylin-eosin (HE) dyeing, or immunity dyeing to visualize the immunity state of a tissue, such as immunohistochemistry (IHC) dyeing. One slice may be dyed by using a plurality of different reagents, or two or more slices (also referred to as adjacent slices) continuously cut out from the same block piece may be dyed by using reagents different from each other.

The microscope 5511 may include a low-resolution image capturing unit for image capturing at low resolution, and a high-resolution image capturing unit for image capturing at high resolution. The low-resolution image capturing unit and the high-resolution image capturing unit may be different optical systems or may be an identical optical system. When the image capturing units are an identical optical system, the resolution of the microscope 5511 may be changed in accordance with an image capturing target.

The glass slide in which the observation object is set is placed on a stage positioned in the angle of view of the microscope 5511. The microscope 5511 first acquires the entire image in the angle of view by using the low-resolution image capturing unit and specifies the region of the observation object from the acquired entire image. Subsequently, the microscope 5511 divides the region in which the observation object exists into a plurality of divided regions of a predetermined size, and sequentially captures images of the divided regions through the high-resolution image capturing unit, thereby acquiring a high-resolution image of each divided region. At switching of a target divided region, the stage may be moved, an image capturing optical system may be moved, or both may be moved. Each divided region may overlap with an adjacent divided region to prevent generation of an uncaptured region and the like due to unintended slipping of the glass slide. The entire image may include identification information for associating the entire image with a patient. The identification information may be, for example, a string or a QR code (registered trademark).

High-resolution images acquired by the microscope 5511 are input to the server 5512. The server 5512 divides each high-resolution image into partial images (hereinafter referred to as tile images) of a smaller size. For example, the server 5512 divides one high-resolution image into 100 tile images of 10 tiles×10 tiles in longitudinal and transverse directions. When adjacent divided regions overlap with each other, the server 5512 may provide stitching processing to high-resolution images adjacent to each other by using a technique such as template matching. In this case, the server 5512 may generate tile images by dividing a high-resolution whole image bonded together by the stitching processing. However, the generation of tile images from a high-resolution image may be performed before the above-described stitching processing.

The server 5512 may generate tile images of a smaller size by further dividing each tile image. The generation of such tile images may be repeated until tile images of a size set as a minimum unit are generated.

Once tile images of the minimum unit are generated in this manner, the server 5512 executes, for every tile image, tile synthesis processing of generating one tile image by synthesizing a predetermined number of adjacent tile images. The tile synthesis processing may be repeated until one tile image is finally generated. Through such processing, a tile image group in a pyramid structure including one or more tile images at each level is generated. In this pyramid structure, the number of pixels of tile images of a layer is equal to the number of pixels of tile images of another layer, but the resolutions thereof are different from each other. For example, when four tile images of 2×2 are synthesized to generate one tile image of the upper layer, the resolution of the tile image of the upper layer is half of the resolution of the tile images of the lower layer used in the synthesis.

When such a tile image group in the pyramid structure is established, it is possible to switch the level of detail of the observation object displayed on the display device, depending on a level to which a display target tile image belongs. For example, a narrow region of the observation object may be displayed in detail when tile images of the lowermost layer are used, and a wider region of the observation object may be coarsely displayed as tile images of an upper layer are used.

The generated tile image group in the pyramid structure is stored in the storage unit (not illustrated) together with, for example, identification information (referred to as tile identification information) with which each tile image is uniquely identifiable. When having received, from another device (for example, the display control device 5513 or the derivation device 5540), a request to acquire a tile image including the tile identification information, the server 5512 transmits the tile image corresponding to the tile identification information to the other device.

Note that a tile image as a pathological image may be generated for each image capturing condition such as a focal length or a dye condition. When a tile image is generated for each image capturing condition, a particular pathological image may be displayed side by side with another pathological image corresponding to an image capturing condition different from a particular image capturing condition and corresponding to a region identical to the region of the particular pathological image. The particular image capturing condition may be specified by a browsing person. When a plurality of image capturing conditions are specified by the browsing person, pathological images corresponding to the respective image capturing conditions and an identical region may be displayed side by side.

The server 5512 may store the tile image group in the pyramid structure in another storage device other than the server 5512, for example, in a cloud server. Part or all of the tile image generation processing as described above may be executed at a cloud server or the like.

The display control device 5513 extracts a desired tile image from the tile image group in the pyramid structure in accordance with an input operation from the user and outputs the tile image to the display device 5514. Through such processing, the user can obtain a sense of observing the observation object by changing the magnification of observation. In other words, the display control device 5513 functions as a virtual microscope. The magnification of virtual observation corresponds to resolution in reality.

Note that a high-resolution image may be captured by any method. A high-resolution image may be acquired by capturing images of divided regions while repeating stopping and moving of the stage, or a high-resolution image on a strip may be acquired by capturing images of divided regions while moving the stage at a predetermined speed. The processing of generating tile images from a high-resolution image is not essential, but the resolution of a high-resolution whole image bonded together by the stitching processing may be changed at stages to generate images among which the resolution is different at stages. In this case as well, a low-resolution image of a wide area to a high-resolution image of a narrow area can be presented at stages to the user.

The medical information system 5530 is what is called an electronic medical record system and stores information related to diagnosis, such as information that identifies a patient, disease information of the patient, examination information and image information used for diagnosis, a diagnosis result, and a prescription. For example, a pathological image obtained through image capturing of an observation object of a patient may be temporarily stored through the server 5512 and then displayed on the display device 5514 by the display control device 5513. A pathologist using the pathological system 5510 performs pathological diagnosis based on the pathological image displayed on the display device 5514. A result of the pathological diagnosis performed by the pathologist is stored in the medical information system 5530.

The derivation device 5540 may execute analysis of the pathological image. This analysis can use a learning model produced by machine learning. The derivation device 5540 may derive, as a result of the analysis, a result of classification of a specific region, a result of identification of a tissue, or the like. In addition, the derivation device 5540 may derive identification results such as cell information, numbers, positions, and luminance information, scoring information thereof, and the like. These pieces of information derived by the derivation device 5540 may be displayed as diagnosis support information on the display device 5514 of the pathological system 5510.

Note that the derivation device 5540 may be a server system constituted by one or more servers (including cloud servers). The derivation device 5540 may be incorporated in, for example, the display control device 5513 or the server 5512 in the pathological system 5510. In other words, various kinds of analysis on a pathological image may be executed in the pathological system 5510.

The technology of the present disclosure is excellently applicable to, for example, the microscope 5511 among the above-described components. Specifically, the technology of the present disclosure may be applied to the low-resolution image capturing unit and/or the high-resolution image capturing unit in the microscope 5511. When the technology of the present disclosure is applied to the low-resolution image capturing unit, specification of the region of an observation object in the entire image can be executed in the low-resolution image capturing unit. In addition, when the technology of the present disclosure is applied to the high-resolution image capturing unit, part or all of the tile image generation processing and the pathological image analysis processing can be executed in the high-resolution image capturing unit. Accordingly, part or all of processes from acquisition of a pathological image to analysis of the pathological image can be executed on-the-fly in the microscope 5511, and thus it is possible to output faster and more appropriate diagnosis support information. For example, partial extraction of a specific tissue and partial outputting of an image with consideration on private information can be executed in the microscope 5511, and thus it is possible to achieve reduction of the image capturing time, reduction of the data amount, reduction of the time of a workflow by a pathologist, and the like.

Note that the above-described configuration is not limited to a diagnosis support system but is also applicable to general biological microscopes such as a confocal microscope, a fluorescence microscope, and a video microscope. An observation object may be a living-body specimen such as a culture cell, a fertilized egg, or a sperm, a living-body material such as a cell sheet or a three-dimensional cellular tissue, or a living body such as a zebrafish or a mouse. The observation object is not limited to a glass slide but may be observed in the state of being stored in a well plate, a petri dish, or the like.

A moving image may be generated from still images of the observation object, which is acquired by using a microscope. For example, a moving image may be generated from still images continuously captured for a predetermined duration, and an image sequence may be generated from still images captured at predetermined intervals. When a moving image is generated from still images in this manner, it is possible to analyze, by using machine learning, dynamic characteristics of the observation object, for example, motion such as pulsation, extension, and migration of a cancer cell, a nerve cell, a myocardial tissue, a sperm, or the like, or a division process of a culture cell or a fertilized egg.

The above-described embodiments and modifications may be combined as appropriate without inconsistency of processing contents.

The effects described in the present specification are merely exemplary and not restrictive, but any other effect may be achieved.

Note that the present technology may be configured as described below.

(1)

An image capturing device comprising:

an image capturing unit mounted on a vehicle and configured to generate image data by performing image capturing of a peripheral region of the vehicle;

a scene recognition unit configured to recognize a scene of the peripheral region based on the image data; and a drive control unit configured to control drive of the image capturing unit based on the scene recognized by the scene recognition unit.

(2)

The image capturing device according to (1), further comprising a signal processing unit configured to execute signal processing on the image data, wherein the scene recognition unit recognizes the scene of the peripheral region based on the image data on which the signal processing is executed by the signal processing unit.

(3)

The image capturing device according to (2), further comprising an output unit configured to output the image data on which the signal processing is executed.

(4)

The image capturing device according to any one of (1) to (3), wherein the scene recognition unit determines whether the scene is a scene for which image data needs to be acquired at high resolution, and the drive control unit controls drive of the image capturing unit to generate image data having a first resolution when the scene recognition unit determines that the scene is a scene for which image data needs to be acquired at high resolution, and controls drive of the image capturing unit to generate image data having a second resolution lower than the first resolution when the scene recognition unit determines that the scene is a scene for which image data does not need to be acquired at high resolution.

(5)

The image capturing device according to (4), wherein the scene recognition unit calculates illuminance in the peripheral region based on the image data and controls drive of the image capturing unit to generate image data having the second resolution when the calculated illuminance exceeds a predetermined threshold.

(6)

The image capturing device according to (4) or (5), wherein the image capturing unit includes a pixel array unit constituted by a plurality of pixels arrayed in a matrix of rows and columns, and the scene recognition unit instructs the drive control unit to read image data from a specific region that is a partial region of the pixel array unit when determining that image data needs to be acquired at high resolution.

(7)

The image capturing device according to (6), wherein the scene recognition unit determines whether the scene is a scene in which a curve is included in the peripheral region, and shifts a position of the specific region in the pixel array unit when determining that the scene is a scene in which a curve is included in the peripheral region.

(8)

The image capturing device according to (4) or (5), further comprising a signal processing unit configured to execute signal processing on the image data, wherein the scene recognition unit recognizes the scene of the peripheral region based on the image data on which the signal processing is executed by the signal processing unit, and when determining that image data needs to be acquired at high resolution, the scene recognition unit causes the signal processing unit to execute processing of extracting, from image data read from the image capturing unit, image data of a specific region that is a part of the read image data.

(9)

The image capturing device according to (8), wherein the scene recognition unit determines whether the scene is a scene in which a curve is included in the peripheral region, and shifts a position of the specific region in the image data when determining that the scene is a scene in which a curve is included in the peripheral region.

(10)

The image capturing device according to (7) or (9), wherein when determining that the scene is a scene in which a curve is included in the peripheral region, the scene recognition unit shifts the specific region based on a shape of the curve.

(11)

The image capturing device according to (4) or (5), wherein the image capturing unit includes a pixel array unit constituted by a plurality of pixels arrayed in a matrix of rows and columns, and the scene recognition unit determines whether the scene is a scene in which a slope is included in the peripheral region, and instructs the drive control unit to read image data from a specific region that is a partial region of the pixel array unit when determining that the scene is a scene in which a slope is included in the peripheral region.

(12)

The image capturing device according to (4) or (5), further comprising a signal processing unit configured to execute signal processing on the image data, wherein the scene recognition unit recognizes the scene of the peripheral region based on the image data on which the signal processing is executed by the signal processing unit, and the scene recognition unit determines whether the scene is a scene in which a slope is included in the peripheral region, and when determining that the scene is a scene in which a slope is included in the peripheral region, the scene recognition unit causes the signal processing unit to execute processing of extracting, from image data read from the image capturing unit, image data of a specific region that is a part of the read image data.

(13)

The image capturing device according to any one of (1) to (12), wherein the image capturing unit includes a first photoelectrical conversion unit, a second photoelectrical conversion unit, a first transfer gate connected with the first photoelectrical conversion unit, a second transfer gate connected with the second photoelectrical conversion unit, and a floating diffusion connected with the first transfer gate and the second transfer gate, and the drive control unit controls drive of the first and the second transfer gates based on the scene recognized by the scene recognition unit.

(14)

The image capturing device according to (13), wherein the image capturing unit includes a pixel array unit constituted by a plurality of pixels arrayed in a matrix of rows and columns, the drive control unit includes a vertical drive circuit configured to control drive of the pixels for each row, and a horizontal drive circuit configured to control drive of the pixels for each column, the vertical drive circuit controls drive of the pixels for each row based on the scene recognized by the scene recognition unit, and the horizontal drive circuit controls drive of the pixel units for each column based on the scene recognized by the scene recognition unit.

(15)

A vehicle control system comprising:

an image capturing unit mounted on a vehicle and configured to generate image data by performing image capturing of a peripheral region of the vehicle;

a scene recognition unit configured to recognize the scene of the peripheral region based on the image data;

a drive control unit configured to control drive of the image capturing unit based on the scene recognized by the scene recognition unit;

an object detection unit configured to detect an object in the peripheral region based on the image data;

a vehicle control signal generation unit configured to generate, based on a result of the detection by the object detection unit, a vehicle control signal for controlling the vehicle; and a vehicle control unit configured to control a vehicle drive unit based on the vehicle control signal.

(16)

The vehicle control system according to (15), further comprising a scene recognition control unit configured to generate a control signal for controlling the scene recognition unit, wherein the scene recognition unit recognizes the scene of the peripheral region based on the image data and the control signal.

(17)

The vehicle control system according to (16), further comprising a vehicle drive sensor configured to detect a state of the vehicle drive unit, wherein the scene recognition control unit generates the control signal based on a result of the detection by the vehicle drive sensor.

(18)

The vehicle control system according to (16) or (17), further comprising a map information storage unit configured to store map information, wherein the scene recognition control unit generates the control signal based on the map information.

REFERENCE SIGNS LIST 1 image capturing device
10 image sensor
11 image capturing unit
12 control unit
13 signal processing unit
14 DSP
15 memory
16 selector
20 application processor
30 cloud server
200 on-board image capturing system
214 scene recognition unit
220 SoC
221 object detection unit
222 vehicle control signal generation unit
223 scene recognition control unit
224 map information storage unit
230 vehicle control device
231 vehicle control unit
232 vehicle drive sensor
233 vehicle drive unit
240 communication unit

The invention claimed is:

1. An image capturing device comprising:
circuitry configured to function as:
an image capturing unit mounted on a vehicle and configured to generate image data by performing image capturing of a peripheral region of the vehicle;
a scene recognition unit configured to recognize a scene of the peripheral region based on the image data; and
a drive control unit configured to control drive of the image capturing unit based on the scene recognized by the scene recognition unit; and
a scene recognition control unit configured to generate a control signal for controlling the scene recognition unit,
wherein the scene recognition unit recognizes the scene of the peripheral region based on the image data and the control signal.

2. The image capturing device according to claim 1, further comprising a signal processing unit configured to execute signal processing on the image data.

3. The image capturing device according to claim 2, further comprising an output unit configured to output the image data on which the signal processing is executed.

4. The image capturing device according to claim 1, wherein
the scene recognition unit determines whether the scene is a scene for which image data needs to be acquired at high resolution, and
the drive control unit
controls drive of the image capturing unit to generate image data having a first resolution when the scene recognition unit determines that the scene is a scene for which image data needs to be acquired at high resolution, and
controls drive of the image capturing unit to generate image data having a second resolution lower than the first resolution when the scene recognition unit determines that the scene is a scene for which image data does not need to be acquired at high resolution.

5. The image capturing device according to claim 4, wherein the scene recognition unit calculates illuminance in the peripheral region based on the image data and controls drive of the image capturing unit to generate image data having the second resolution when the calculated illuminance exceeds a predetermined threshold.

6. The image capturing device according to claim 4, wherein
the image capturing unit includes a pixel array unit constituted by a plurality of pixels arrayed in a matrix of rows and columns, and
the scene recognition unit instructs the drive control unit to read image data from a specific region that is a partial region of the pixel array unit when determining that image data needs to be acquired at high resolution.

7. The image capturing device according to claim 6, wherein the scene recognition unit determines whether the scene is a scene in which a curve is included in the peripheral region, and shifts a position of the specific region in the pixel array unit when determining that the scene is a scene in which a curve is included in the peripheral region.

8. The image capturing device according to claim 4, further comprising a signal processing unit configured to execute signal processing on the image data, wherein
when determining that image data needs to be acquired at high resolution, the scene recognition unit causes the signal processing unit to execute processing of extracting, from image data read from the image capturing unit, image data of a specific region that is a part of the read image data.

9. The image capturing device according to claim 8, wherein the scene recognition unit determines whether the scene is a scene in which a curve is included in the peripheral region, and shifts a position of the specific region in the image data when determining that the scene is a scene in which a curve is included in the peripheral region.

10. The image capturing device according to claim 7, wherein when determining that the scene is a scene in which a curve is included in the peripheral region, the scene recognition unit shifts the specific region based on a shape of the curve.

11. The image capturing device according to claim 4, wherein
the image capturing unit includes a pixel array unit constituted by a plurality of pixels arrayed in a matrix of rows and columns, and
the scene recognition unit determines whether the scene is a scene in which a slope is included in the peripheral region, and instructs the drive control unit to read image data from a specific region that is a partial region of the pixel array unit when determining that the scene is a scene in which a slope is included in the peripheral region.

12. The image capturing device according to claim 4, further comprising a signal processing unit configured to execute signal processing on the image data, wherein
the scene recognition unit determines whether the scene is a scene in which a slope is included in the peripheral region, and when determining that the scene is a scene in which a slope is included in the peripheral region, the scene recognition unit causes the signal processing unit to execute processing of extracting, from image data read from the image capturing unit, image data of a specific region that is a part of the read image data.

13. The image capturing device according to claim 1, wherein
the image capturing unit includes
a first photoelectrical conversion unit,
a second photoelectrical conversion unit,
a first transfer gate connected with the first photoelectrical conversion unit,
a second transfer gate connected with the second photoelectrical conversion unit, and
a floating diffusion connected with the first transfer gate and the second transfer gate, and
the drive control unit controls drive of the first and the second transfer gates based on the scene recognized by the scene recognition unit.

14. The image capturing device according to claim 13, wherein
the image capturing unit includes a pixel array unit constituted by a plurality of pixels arrayed in a matrix of rows and columns,
the drive control unit includes
a vertical drive circuit configured to control drive of the pixels for each row, and
a horizontal drive circuit configured to control drive of the pixels for each column,
the vertical drive circuit controls drive of the pixels for each row based on the scene recognized by the scene recognition unit, and
the horizontal drive circuit controls drive of the pixel units for each column based on the scene recognized by the scene recognition unit.

15. A vehicle control system comprising:
circuitry configured to function as:
an image capturing unit mounted on a vehicle and configured to generate image data by performing image capturing of a peripheral region of the vehicle;
a scene recognition unit configured to recognize the scene of the peripheral region based on the image data;
a drive control unit configured to control drive of the image capturing unit based on the scene recognized by the scene recognition unit;
an object detection unit configured to detect an object in the peripheral region based on the image data;
a vehicle control signal generation unit configured to generate, based on a result of the detection by the object detection unit, a vehicle control signal for controlling the vehicle;
a vehicle control unit configured to control a vehicle drive unit based on the vehicle control signal; and
a scene recognition control unit configured to generate a control signal for controlling the scene recognition unit,
wherein the scene recognition unit recognizes the scene of the peripheral region based on the image data and the control signal.

16. The vehicle control system according to claim 15, further comprising a vehicle drive sensor configured to detect a state of the vehicle drive unit, wherein
the scene recognition control unit generates the control signal based on a result of the detection by the vehicle drive sensor.

17. The vehicle control system according to claim 15, further comprising a map information storage unit configured to store map information, wherein
the scene recognition control unit generates the control signal based on the map information.

* * * * *